United States Patent
Zhao et al.

(10) Patent No.: US 11,717,261 B2
(45) Date of Patent: Aug. 8, 2023

(54) FLOATING MECHANISM AND ULTRASONIC DIAGNOSTIC APPARATUS

(71) Applicant: SHENZHEN MINDRAY BIO-MEDICAL ELECTRONICS CO., LTD., Guangdong (CN)

(72) Inventors: Yanqun Zhao, Shenzhen (CN); Rongfu Yang, Shenzhen (CN); Zhiwu Chen, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 711 days.

(21) Appl. No.: 16/613,500

(22) PCT Filed: May 15, 2017

(86) PCT No.: PCT/CN2017/084380
§ 371 (c)(1),
(2) Date: Feb. 25, 2021

(87) PCT Pub. No.: WO2018/209514
PCT Pub. Date: Nov. 22, 2018

(65) Prior Publication Data
US 2022/0370039 A1    Nov. 24, 2022

(51) Int. Cl.
*F16M 11/04* (2006.01)
*A61B 8/00* (2006.01)

(52) U.S. Cl.
CPC ............ *A61B 8/4405* (2013.01); *A61B 8/462* (2013.01); *F16M 11/045* (2013.01);
(Continued)

(58) Field of Classification Search
CPC .... F16M 11/10; F16M 11/045; F16M 11/046; F16M 11/048; F16M 11/2092;
(Continued)

(56) References Cited

U.S. PATENT DOCUMENTS 201,925 A * 4/1878 King ...................... B60N 2/502
5/255
6,905,101 B1 * 6/2005 Dittmer .................. F16M 11/10
248/125.7
(Continued)

FOREIGN PATENT DOCUMENTS

CN    101303901 A    11/2008
CN    202284630 U    6/2012
(Continued)

OTHER PUBLICATIONS

PCT International Preliminary Reporton Patentability dated Nov. 28,2019, issued in related International Application No. PCT/CN2017/084380, with English translation (11 pages).
(Continued)

*Primary Examiner* — Patrick D Hawn
(74) *Attorney, Agent, or Firm* — Sheppard Mullin Richter & Hampton LLP

(57) ABSTRACT

A floating mechanism (300) and an ultrasonic diagnostic apparatus. The floating mechanism (300) and the ultrasonic diagnostic apparatus can implement the direct superposition of lifting movements and rotational movements, so that the floating mechanism (300) can move in more directions. In addition, a lifting structure and a rotation structure in the floating mechanism (300) are integrally linked in design, accordingly, the link performance is good, the response is fast, the occupied space is small, and the operation range is great.

11 Claims, 16 Drawing Sheets

(52) U.S. Cl.
CPC ......... *F16M 11/046* (2013.01); *F16M 11/048* (2013.01); *F16M 2200/047* (2013.01); *F16M 2200/066* (2013.01)

(58) Field of Classification Search
CPC ......... F16M 11/2014; F16M 2200/061; F16M 2200/047; F16M 2200/066; Y10S 248/919; Y10S 248/923; A61B 8/4405; A61B 8/462
See application file for complete search history.

(56) References Cited

U.S. PATENT DOCUMENTS

| | | | | |
|---|---|---|---|---|
| 7,398,950 | B2 * | 7/2008 | Hung | F16M 13/027 248/921 |
| 7,487,943 | B1 * | 2/2009 | Gillespie | F16M 11/10 248/920 |
| 7,571,883 | B2 * | 8/2009 | Van Groesen | F16M 13/02 248/920 |
| 8,052,101 | B2 * | 11/2011 | Asakura | F16M 11/2014 248/921 |
| 8,245,990 | B2 * | 8/2012 | Huang | F16M 13/02 248/920 |
| 8,693,172 | B2 * | 4/2014 | Russell | F16M 11/085 361/679.01 |
| 8,888,062 | B2 * | 11/2014 | Novin | F16M 11/12 361/679.01 |
| 9,004,430 | B2 * | 4/2015 | Conner | H04N 5/655 248/920 |
| 9,121,543 | B2 * | 9/2015 | Dittmer | F16M 13/02 |
| 9,316,346 | B2 | 4/2016 | Lau et al. | |
| 9,404,618 | B2 * | 8/2016 | Brown | F16M 11/2092 |
| 9,433,293 | B2 * | 9/2016 | Gross | F16M 13/02 |
| 9,861,339 | B2 | 1/2018 | Jin et al. | |
| 10,154,729 | B2 * | 12/2018 | Blackburn | F16M 13/02 |
| 10,299,759 | B2 | 5/2019 | Messina et al. | |
| 10,323,786 | B2 * | 6/2019 | HÖRndler | F16M 11/2064 |
| 10,563,811 | B2 * | 2/2020 | Pei | F16M 11/2085 |
| 10,695,028 | B2 * | 6/2020 | Zhao | F16M 11/048 |
| 11,112,057 | B2 * | 9/2021 | Janechek | F16M 11/28 |
| 11,215,313 | B1 * | 1/2022 | Beil | F16M 11/2014 |
| 11,536,416 | B2 * | 12/2022 | Anderson | F16M 11/2092 |
| 2003/0025054 | A1 | 2/2003 | Toennesland et al. | |
| 2008/0001048 | A1 * | 1/2008 | Woo | F16M 11/18 248/276.1 |
| 2008/0234577 | A1 | 9/2008 | Murkowski et al. | |
| 2009/0034178 | A1 * | 2/2009 | Le | F16M 11/2064 361/679.27 |
| 2009/0272870 | A1 | 11/2009 | Asakura et al. | |
| 2013/0032682 | A1 * | 2/2013 | Bell | F16M 11/10 248/277.1 |
| 2013/0327911 | A1 * | 12/2013 | Russell | F16M 11/08 248/276.1 |
| 2016/0319986 | A1 | 11/2016 | Hörndler | |
| 2021/0332936 | A1 * | 10/2021 | Lyu | F16M 11/18 |

FOREIGN PATENT DOCUMENTS

| | | |
|---|---|---|
| CN | 202419054 U | 9/2012 |
| CN | 103006257 A | 4/2013 |
| CN | 202859150 A | 4/2013 |
| CN | 103629502 A | 3/2014 |
| CN | 104869909 A | 8/2015 |
| CN | 105078508 A | 11/2015 |
| CN | 204778693 U | 11/2015 |
| CN | 205126424 U | 4/2016 |
| CN | 205144598 U | 4/2016 |
| CN | 106051392 A | 10/2016 |
| CN | 205938403 U | 2/2017 |
| DE | 102015005505 B3 | 6/2016 |
| JP | 2007-159930 A | 6/2007 |
| JP | 2017-006476 A | 1/2017 |
| KR | 2015-0018068 A | 2/2015 |

OTHER PUBLICATIONS

First Search dated May 11, 2021, issued in related Chinese Application No. 201780079220.X (2 pages).
First Office Action dated May 20, 2021, issued in related Chinese Application No. 201780079220.X, with English machine translation (27 pages).
PCT International Search Report and the Written Opinion dated Jan. 29, 2018, issued in related International Application No. PCT/CN2017/084380, with English machine translation of ISR (12 pages).
Supplementary Search dated Nov. 23, 2021, issued in related Chinese Application No. 201780079220.X (2 pages).
Second Office Action dated Dec. 1, 2021, issued in related Chinese Application No. 201780079220.X, with English machine translation (16 pages).
Supplementary Search dated Feb. 18, 2022, issued in related Chinese Application No. 201780079220.X (1 page).

* cited by examiner

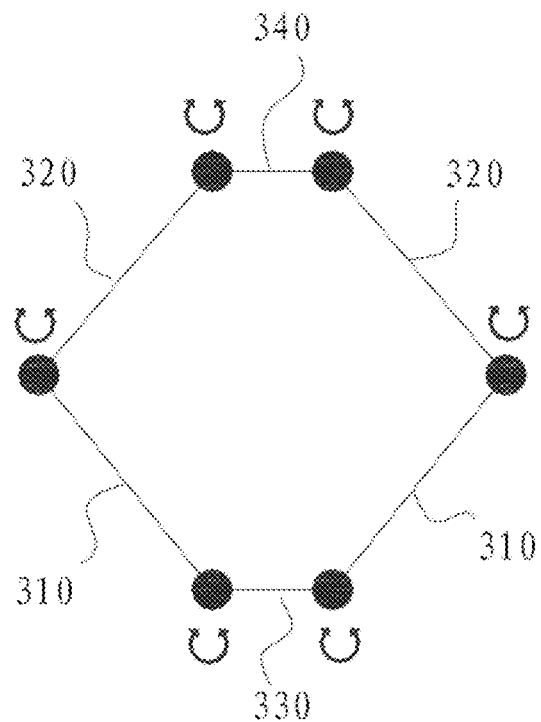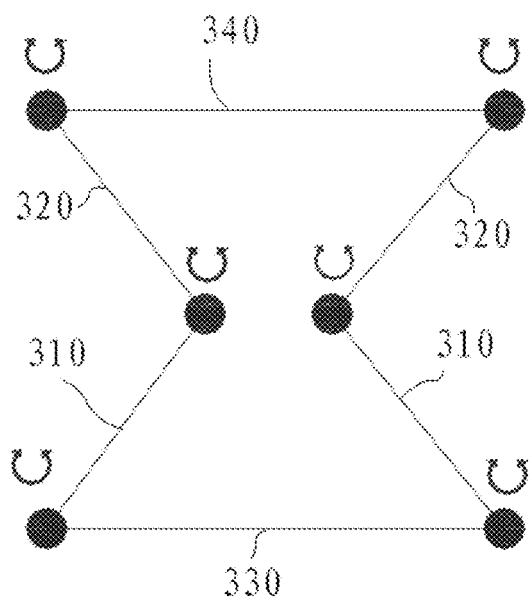
FIG. 20a  FIG. 20b
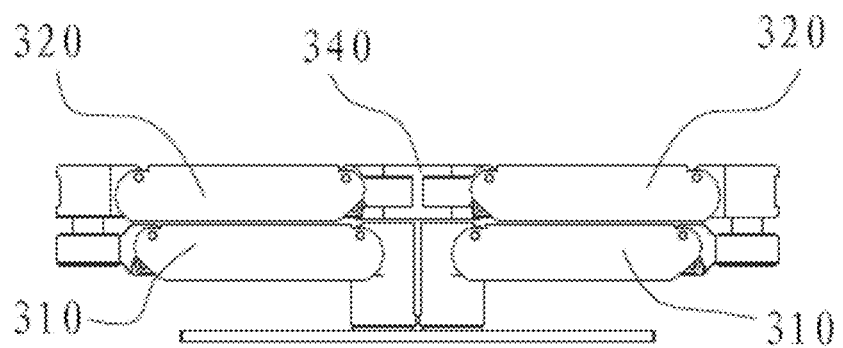
FIG. 21a

FLOATING MECHANISM AND ULTRASONIC DIAGNOSTIC APPARATUS

This application is a national phase application of International Patent Application No. PCT/CN2017/084380, filed on May 15, 2017, and entitled "FLOATING MECHANISM AND ULTRASONIC DIAGNOSTIC APPARATUS." The content of the above application is incorporated herein by reference in its entirety.

TECHNICAL FIELD

The present disclosure relates to a mechanical structure, in particular to a floating mechanism capable of multi-directional movement.

BACKGROUND

When a medical staff operates a medical device with a control panel (e.g., an ultrasound diagnostic apparatus), it is usually desired that the control panel is able to be moved flexibly based on the needs of operation, diagnosis and treatment, especially when performing the examinations in different positions. That is, it is desired that the control panel is able to be moved up and down, back and forth movement, and left and right, and be rotated left and right, etc. (full floating operation). Therefore, it is desired that the floating device of the control panel can provide such a function.

There are two usual floating structures of the control panel. The first one includes an independent rising-and-lowering mechanism (in the vertical plane) and an independent back-and-forth translation and rotation structure (in the horizontal plane). In this floating structure, the lifting motion and the back-and-forth and rotation motion are respectively realized by two independent mechanisms, and the rising-and-lowering mechanism occupies a large space. The second one includes an independent rising-and-lowering mechanism (in the vertical plane) and an independent frog leg structure (in the horizontal plane). The frog leg structure is a modified parallel four-bar structure whose fixed end is formed by two rotating fulcrums so as to drive the four arms, and the control panel is fixed to the ends of the two arms, so as to achieve the forward and backward translation, left and right translation and rotation within a certain range. In this floating structure, the lifting motion and the translation and rotation motion in the horizontal plane need to be achieved by separate operation, and there is no linkage.

SUMMARY

In the present disclosure, a new type of floating mechanism and an ultrasound diagnostic apparatus using the same may be provided so as to achieve the multi-directional floating of the components.

In one embodiment, an ultrasound diagnostic apparatus is provided, which may include a main body, a control panel and a display, and further include at least one connection rod assembly connected between a first component and a second component. The first component and the second component may be any two of the control panel, the main body and the display. The connection rod assembly may include:

a first support seat connected to the first component;

a first connection arm, where one end of the first connection arm is connected to the first support seat through a first rotation pair and is able to be rotated around a first rotation axis relative to the first support seat through the first rotation pair;

a first connection seat, where the other end of the first connection arm is connected to the first connection seat through a second rotation pair and is able to be rotated around a second rotation axis relative to the first connection seat through the second rotation pair;

a second connection seat connected to the first connection seat through a third rotation pair and being able to be rotated around a third rotation axis relative to the first connection seat through the third rotation pair;

a second connection arm, where one end of the second connection arm is connected to the second connection seat through a fourth rotation pair and is able to be rotated around a fourth rotation axis relative to the second connection seat through the fourth rotation pair; and a second support seat, where the other end of the second connection arm is connected to the second support seat through a fifth rotation pair and is able to be rotated around a fifth rotation axis relative to the second support seat through the fifth rotation pair;

where the second support seat is connected to the second component.

In one embodiment, the first support seat may be connected to the first component through a sixth rotation pair and be able to be rotated around a sixth rotation axis relative to the first component through the sixth rotation pair.

In one embodiment, the second support seat may be connected to the second component through a seventh rotation pair and be able to be rotated around a seventh rotation axis relative to the second component through the seventh rotation pair.

In one embodiment, an ultrasound diagnostic apparatus is provided, which may include a main body, a control panel and a display, and further include a first connection rod assembly and a second connection rod assembly connected between a first component and a second component. The first component and the second component may be any two of the control panel, the main body and the display. Each connection rod assembly may include:

a first support seat connected to the first component through a sixth rotation pair and being able to be rotated around a sixth rotation axis relative to the first component through the sixth rotation pair;

a first connection arm, where one end of the first connection arm is connected to the first support seat through a first rotation pair and is able to be rotated around a first rotation axis relative to the first support seat through the first rotation pair;

a first connection seat, where the other end of the first connection arm is connected to the first connection seat through a second rotation pair and is able to be rotated around a second rotation axis relative to the first connection seat through the second rotation pair;

a second connection seat connected to the first connection seat through a third rotation pair and being able to be rotated around a third rotation axis relative to the first connection seat through the third rotation pair;

a second connection arm, where one end of the second connection arm is connected to the second connection seat through a fourth rotation pair and is able to be rotated around a fourth rotation axis relative to the second connection seat through the fourth rotation pair; and a second support seat, where the other end of the second connection arm is connected to the second support seat through a fifth rotation pair and is able to be rotated around a fifth rotation axis relative to the second support seat through the fifth rotation pair;

where the second support seat is connected to the second component through a seventh rotation pair and is able to be rotated around a seventh rotation axis relative to the second component through the seventh rotation pair.

In one embodiment, the first support seat of the first connection rod assembly and the first support seat of the second connection rod assembly are separate, and are connected to the first component at a predetermined distance; and/or, the second support seat of the first connection rod assembly and the second support seat of the second connection rod assembly are separate, and are connected to the second component at a predetermined distance.

In one embodiment, the first rotation axis and the second rotation axis are parallel to each other.

In one embodiment, the fourth rotation axis and the fifth rotation axis are parallel to each other.

In one embodiment, the third rotation axis and the second rotation axis are perpendicular to each other.

In one embodiment, the third rotation axis and the fourth rotation axis are perpendicular to each other.

In one embodiment, the sixth rotation axis and the third rotation axis are parallel to each other.

In one embodiment, the seventh rotation axis and the third rotation axis are parallel to each other.

In one embodiment, the third rotation axis of the first connection rod assembly and the third rotation axis of the second connection rod assembly are parallel to each other.

In one embodiment, the sixth rotation axis of the first connection rod assembly and the sixth rotation axis of the second connection rod assembly are parallel to each other.

In one embodiment, the seventh rotation axis of the first connection rod assembly and the seventh rotation axis of the second connection rod assembly are parallel to each other.

In one embodiment, a floating mechanism is provided, which may include at least one connection rod assembly. The connection rod assembly may include:

a first rising-and-lowering mechanism mounted on a first component, where the first rising-and-lowering mechanism is provided with a rising-and-lowering mechanism that enables one end of the first rising-and-lowering mechanism to lift relative to the first component in a vertical direction; and a second rising-and-lowering mechanism supporting a second component, where one end of the second rising-and-lowering mechanism is rotatably connected to the first rising-and-lowering mechanism and the other end of the second rising-and-lowering mechanism is able to lift relative to the first rising-and-lowering mechanism in a vertical direction.

In one embodiment, a floating mechanism is provided, which may include two connection rod assemblies. Each connection rod assembly may include:

a first rising-and-lowering mechanism mounted on a first component, where the first rising-and-lowering mechanism is provided with a rising-and-lowering mechanism that enables one end of the first rising-and-lowering mechanism to lift relative to the first component in a vertical direction; and a second rising-and-lowering mechanism supporting a second component, where one end of the second rising-and-lowering mechanism is rotatably connected to the first rising-and-lowering mechanism and the other end of the second rising-and-lowering mechanism is able to lift relative to the first rising-and-lowering mechanism in a vertical direction.

In one embodiment, the second rising-and-lowering mechanism may include a second upper bracket, a second support seat, a second lower bracket and a second connection seat that are sequentially rotatably connected to form a four-bar structure, and the second connection seat is rotatably connected to the first rising-and-lowering mechanism.

In one embodiment, the first rising-and-lowering mechanism may include a first upper bracket, a first support seat, a first lower bracket and a first connection seat that are sequentially rotatably connected to form a four-bar structure, and the second connection seat is rotatably connected to the first connection seat.

In one embodiment, at least one of the first connection seat and the second connection seat is provided with a first limiting groove that is arranged in an arc around a rotation center line between the first connection seat and the second connection seat, and the other one of the first connection seat and the second connection seat is provided with a first limiting pin that cooperates with the first limiting groove so as to limit a relative rotation angle between the first connection seat and the second connection seat.

In one embodiment, the first connection seat is provided with a first lug, the first lug is provided with a first shaft hole that is used for a rotation connection with the second connection seat, the first limiting groove is provided at a periphery of the first shaft hole, the second connection seat is installed on the first shaft hole, and the first limiting pin is fixedly installed on the second connection seat.

In one embodiment, the floating mechanism may further include a mounting seat, where the first rising-and-lowering mechanism is rotatably connected to the mounting seat and a rotation center line of the first rising-and-lowering mechanism relative to the mounting seat is consistent with a direction of the lifting movement of the first rising-and-lowering mechanism.

In one embodiment, the floating mechanism may further include a mounting seat, where the first support seat is rotatably connected to the mounting seat so as to enable the first rising-and-lowering mechanism and the second rising-and-lowering mechanism to rotate relative to the mounting seat as a whole.

In one embodiment, at least one of the mounting seat and the first support seat is provided with a second shaft hole, the other one of the mounting seat and the first support seat is provided with a second rotation shaft, and the second rotation shaft cooperates with the second shaft hole so as to enable the first support seat to rotate relative to the mounting seat.

In one embodiment, at least one of the mounting seat and the first support seat is provided with a second limiting groove that is arranged in an arc around a rotation center line between the mounting seat and the first support seat, the other one of the mounting seat and the first support seat is provided with a second limiting pin, and the second limiting pin cooperates with the second limiting groove to limit a relative rotation angle between the mounting seat and the first support seat.

In one embodiment, the floating mechanism may further include a damping pin that passes through a hole wall of the second shaft hole and applies a damping force on the second rotation shaft.

In one embodiment, the second rotation shaft is provided on the mounting seat, the second shaft hole is provided on the first support seat, the first support seat is arranged on the second rotation shaft upside down, and the damping pin is inserted into the second shaft hole from an outer wall of the first support seat.

In one embodiment, the floating mechanism may further include a fixation seat for connecting the second component, where the second rising-and-lowering mechanism is rotatably connected to the fixation seat and a rotation center line of the second rising-and-lowering mechanism relative the fixation seat is consistent with a direction of the lifting movement of the second rising-and-lowering mechanism.

In one embodiment, the floating mechanism may further include a fixation seat for connecting the first component, where the second support seat is rotatably connected to the fixation seat.

In one embodiment, at least one of the second support seat and the fixation seat is provided with a third limiting groove that is arranged in an arc around a rotation center line between the second support seat and the fixation seat, the other one of the second support seat and the fixation seat is provided with a third limiting pin, and the third limiting pin cooperates with the third limiting groove to limit a relative rotation angle between the second support seat and the fixation seat.

In one embodiment, the second connection seat is provided with a second lug, the second lug is provided with a third shaft hole that is used for a rotation connection with the fixation seat, the third limiting groove is provided at a periphery of the third shaft hole, the fixation seat is installed on the third shaft hole, and the third limiting pin is fixedly installed on the fixation seat.

In one embodiment, the first rising-and-lowering mechanism and/or the second rising-and-lowering mechanism is provided with a damping balance compensation system that provides a damping balance force for the four-bar structure formed by the first rising-and-lowering mechanism and/or the second rising-and-lowering mechanism.

In one embodiment, an ultrasound diagnostic apparatus is provided, which may include a main body, a control panel and a display, and further include a floating mechanism connected between a first component and a second component. The floating mechanism is any one of the floating mechanisms above, and the first component and the second component may be any two of the control panel, the main body and the display.

In one embodiment, the ultrasound diagnostic apparatus may include at least two of the floating mechanisms, where at least one of the floating mechanisms is arranged between the main body and the control panel and at least one of the floating mechanisms is arranged between the display and the control panel.

Since the connection rod assembly or the floating mechanism can achieve the direct superimposition of the lifting motion and the rotation motion, the movement in more directions can be achieve. Moreover, the rising-and-lowering mechanism and the rotation structure are designed as being moved in linkage, which leads to good linkage, quick response, small space and large operation range.

BRIEF DESCRIPTION OF THE DRAWINGS

FIG. 19 and FIG. 20 schematically show the modifications of the rising-and-lowering mechanisms in the floating mechanism in one embodiment;

DETAILED DESCRIPTION

The present disclosure will be described in detail below with reference to the drawings and the specific embodiments, in which similar elements in different embodiments are assigned with similar reference number. In the following embodiments, many details are described so as to facilitate the understanding to the present disclosure. However, those skilled in the art can easily recognize that, in different situations, some of the features can be omitted or can be replaced by other elements, materials or methods. In some cases, some operations in the present disclosure are not shown or described in the specification so as to avoid the core part of the present disclosure being overwhelmed by too many descriptions. For those skilled in the art, the detailed description of these operations is not necessary. They can fully understand these operations according to the description in the specification and the general technical knowledge in the field.

In addition, the features, operations or characteristics described in the specification may be combined in any appropriate manner to form various embodiments. Furthermore, the sequence of the steps or actions in the described methods can also be replaced or adjusted in a manner obvious to those skilled in the art. Therefore, the various sequences in the specification and the drawings are only for clearly describing a certain embodiment, but not mean a necessary sequence unless otherwise stated that a certain sequence must be followed.

The serial numbers in the present disclosure, such as "first", "second", etc., are used to distinguish the described objects, but not have any sequential or technical meaning. The "connection" or "coupling" mentioned in the present disclosure, unless otherwise specified, will include direct and indirect connection (coupling).

Embodiment 1

In this embodiment, an ultrasound diagnostic apparatus is provided.

Figure 1:
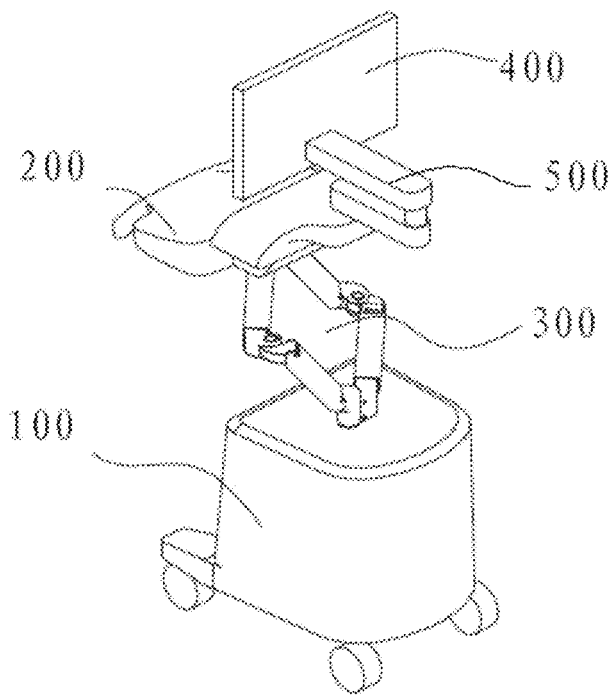
FIG. 1 schematically shows an ultrasound diagnostic apparatus in one embodiment of the present disclosure.
Figure 2:
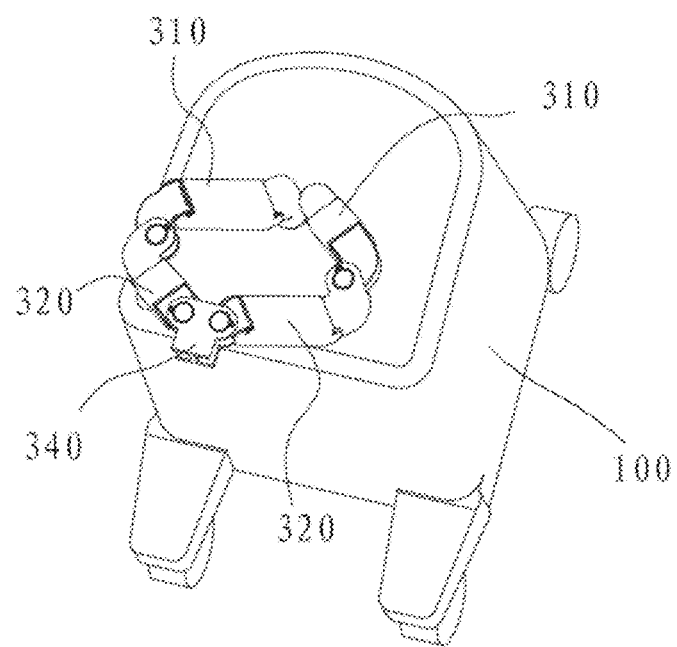
FIG. 2 is a schematic diagram of the cooperation between the floating mechanism and the main body in one embodiment.

Referring to FIG. 1, the ultrasound diagnostic apparatus may include a main body 100, a control panel 200, a floating mechanism 300, a display 400 and a support arm 500. FIG. 1 shows only the structure related to the present embodiment.

The control panel 200 may generally be provided with buttons, knobs, etc., and the user can operate the ultrasound diagnostic apparatus through the control panel 200. One end of the support arm 500 may be connected to the control panel 200, and the display 400 may be fixedly connected to the other end of the support arm 500 away from the control panel 200, and be configured to display the information of the processing process, the results of the processing or other information.

Referring to FIG. 1, the floating mechanism may connect the main body 100 and the control panel 200. The control panel 200 may be installed on the main body 100 through the floating mechanism 300 and achieve the movement in multiple directions. In other embodiments, the floating mechanism 300 may be arranged at other positions on the ultrasound diagnostic apparatus, but not limited to achieve of the floating movement of the control panel 200. For example, the floating mechanism 300 may be arranged to achieve the floating of the display 400 or other movable parts that need to be floated, which will not be limited herein.

Generally, the floating mechanism may be used to connect a first component and a second component. The first component and the second component may be any component that is desired to be floated. For example, in an ultrasound diagnostic apparatus, it can be used to connect the display, the control panel or the main body, etc.

In one embodiment, as shown in FIG. 1, the floating mechanism may connect the main body 100 and the control panel 200. In this case, the first component may be the main body 100, and the second component may be the control panel 200. Alternatively, the first component may be the control panel 200, and the second component may be the main body 100.

In other embodiments, the floating mechanism may connect the control panel 200 and the display 400. In this case, the first component may be the control panel 200, and the second component may be the display 400 accordingly. Alternatively, the first component may be the display 400, the second component may be the control panel 200.

In other embodiments, the floating mechanism may directly connect the main body 100 and the display 400. In this case, the first component may be the main body 100, and the second component may be the display 400. Alternatively, the first component may be the display 400, and the second component may be the main body 100.

Furthermore, in other embodiments, the first component and/or the second component may also be other connection arm, support arm, connection rod or other intermediate connection elements, but not limited to the target element to be connected.

Figure 3:
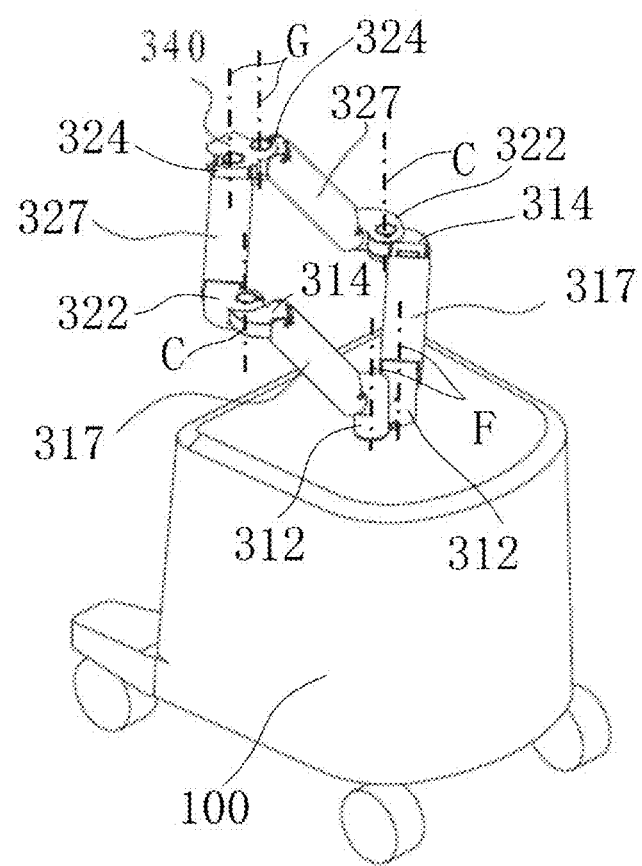
FIG. 3 is a schematic diagram of the embodiment shown in FIG. 2 in another perspective.
Figure 4:
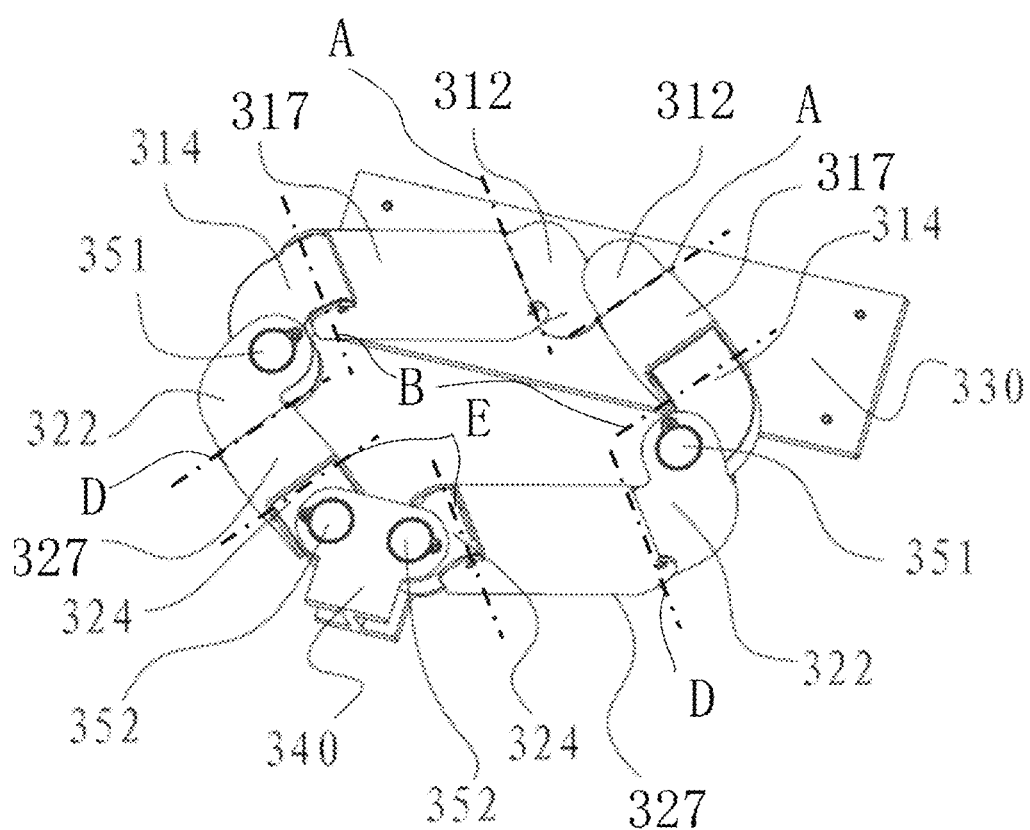
FIG. 4 schematically shows a floating mechanism in one embodiment.

Referring to FIG. 3 and FIG. 4, in one embodiment, the floating mechanism 300 may include one or more connection rod assemblies. Each connection rod assembly may include a first support seat 312, a first connection arm 317 and a first connection seat 314.

One end of the first connection arm 317 may be connected to the first support seat 312 through a first rotation pair, and be able to be rotated around a first rotation axis A with respect to the first support seat 312 through the first rotation pair. The other end of the first connection arm 317 may be connected to the first connection seat 314 through a second rotation pair, and be able to be rotated around a second rotation axis B with respect to the first connection seat 314 through the second rotation pair.

In this way, the first support seat 312, the first connection arm 317 and the first connection seat 314 may form a structure which is able to rise and fall, such that the first connection seat 314 can rise and fall relative to the first support seat 312.

In addition, referring to FIG. 3 and FIG. 4, each connection rod assembly may further include a second connection seat 322, a second connection arm 327 and a second support seat 324.

The second connection seat 322 may be connected to the first connection seat 314 through a third rotation pair, and be able to be rotated around a third rotation axis C relative to the first connection seat 314 through the third rotation pair. One end of the second connection arm 327 may be connected to the second connection seat 322 through a fourth rotation pair, and be able to be rotated around a fourth rotation axis D relative to the second connection seat 322 through the fourth rotation pair. The other end of the second connection arm 327 may be connected to the second support seat 324 through a fifth rotation pair, and be able to be rotated around a fifth rotation axis E relative to the second support seat 324 through the fifth rotation pair.

In this way, the second connection seat 322, the second connection arm 327 and the second support seat 324 may form a structure which is able to rise and fall, such that the second support seat 324 can rise and fall relative to the second connection seat 322. Further through the rising-and-lowering mechanism formed by the first support seat 312, the first connection arm 317 and the first connection seat 314 and the rotation structure between the second connection seat 322 and the first connection seat 314, the floating mechanism 300 can achieve the movement in more directions. Furthermore, the rising-and-lowering mechanism and the rotation structure of the floating mechanism are designed as being moved in linkage, which have good linkage, quick response, small space and large operating range.

In the embodiments above, the first connection arm 317 and the second connection arm 327 may be a single component formed by a rod-shaped element, such as a connection rod. Alternatively, the first connection arm 317 and the second connection arm 327 may be a component formed by multiple elements. For example, referring to FIG. 5, in some embodiments, the first connection arm 317 may include a first upper bracket 311 and a first lower bracket 313. Similarly, in some embodiments, the second connection arm 327 may include a second upper bracket 321 and a second lower bracket 323. Of course, the first connection arm 317 and the second connection arm 327 may also adopt other forms of structure.

The rotatable connection between the components above may be achieved by rotation pairs. The rotation pair (including other rotation pairs in the embodiments) may be any suitable rotation pair mechanism, such as the rotation pair formed by a limiting pin and a pin hole or the rotation pair formed by a rotation seat and a shaft. Some examples of the rotation pairs will be described in detail below with reference to the drawings. However, it can be easily understood that the rotation pair will not be limited to the examples described in detail below.

Referring to FIG. 4, in some embodiments, the first rotation axis A and the second rotation axis B may be parallel to each other, such that the rotation movements of the first connection arm 317 respectively relative to the first support seat 312 and the first connection seat 314 are in the same plane or in parallel planes, so as to reduce the interference between the two rotation movements and enable the two rotation movements to be well superimposed to achieve more position changes.

Referring to FIG. 4, in some embodiments, the fourth rotation axis D and the fifth rotation axis E may be parallel to each other, such that the rotation movements of the second connection arm 327 respectively relative to the second support seat 324 and the second connection seat 322 are in the same plane or in parallel planes, so as to reduce the interference between the two rotation movements and enable the two rotation movements to be well superimposed to achieve more position changes.

Referring to FIG. 3 and FIG. 4, in some embodiments, the third rotation axis C and the second rotation axis B may be perpendicular to each other, such that the rotation movement of the second connection seat 322 on the first connection seat 314 may be perpendicular to the lifting movement of the first connection seat 314 relative to the first support seat 312, so as to reduce the mutual interference of the lifting movement and the rotation movement and ensure that the floating mechanism is easier to be operated and easier to be moved to the desired position.

In some embodiments, the third rotation axis C and the fourth rotation axis D may be perpendicular to each other (it may be understood that in this case the fourth rotation axis D and the second rotation axis B may or may not be parallel to each other), such that the lifting movement of the second connection arm 327 on the second connection seat 322 and the rotation movement of the second connection seat 322 relative to the first connection seat 314 may be perpendicular to each other, so as to facilitate the superposition of the two lifting movements, reduce the interference between the movements and ensure that the floating mechanism is easier to be operated and easier to be moved to the desired position.

In the present disclosure, when two rotation axes are "perpendicular to each other", it may mean that, when the two rotation axes are in the same plane, they are perpendicular to each other; and when the two rotation axes are not in the same plane, they are perpendicular to each other in space, that is, the projection of one rotation axis on the plane in which the other rotation axis is located is perpendicular to said other rotation axis.

In the present disclosure, when rotation axes "intersect with" each other, it may mean that, when the two rotation axes are in the same plane, they intersect with each other; and when the two rotation axes are not in the same plane, the projection of one rotation axis on the plane in which the other rotation axis is located intersects with said other rotation axis.

The first support seat 312 may also be rotatably connected to the first component. For example, referring to FIG. 3 and FIG. 4, in one embodiment, the first support seat 312 may be connected to the first component (in the embodiment shown in the figure, the main body 100) through a sixth rotation pair, and be able to be rotated around a sixth rotation axis F through the sixth rotation pair. The rotation structure with the sixth rotation axis F can increase the degree of freedom between the first component and the second component, such that the first component may have more position changes and movement paths relative to the second component.

Referring to FIG. 3 and FIG. 4, in some embodiments, the sixth rotation axis F and the third rotation axis C may be parallel to each other, such that the rotation direction of the first support seat 312 on the first component and the rotation directions of the first connection seat 314 and the second connection seat 322 may be in the same plane or parallel to each other, so as to reduce the mutual interference of the rotation movements. Thereby, the rotation movements can be maximally superimposed. Therefore, a better rotation effect can be achieved and more position changes can be realized.

The second support seat 324 may also be rotatably connected to the second component. For example, referring to FIG. 1, FIG. 3 and FIG. 4, in one embodiment, the second support seat 324 may be connected to the second component through a seventh rotation pair (in the embodiment shown in FIG. 1, the second component may be the control panel 200, which may, for example, be connected to a fixation seat 340, so as to be connected to the control panel 200 through the fixation seat 340), and may be able to be rotated about a seventh rotation axis G relative to the second component through the seventh rotation pair. With the structure that may be rotated around the seventh rotation axis G, the degree of freedom between the first component and the second component may be increased, such that the first component may have more position changes and movement paths relative to the second component.

Referring to FIG. 3 and FIG. 4, in some embodiments, the seventh rotation axis G and the third rotation axis C may be parallel to each other, such that the rotation direction of the second support seat 324 on the second component and the rotation directions of the first connection seat 314 and the second connection seat 322 may be in the same plane or parallel to each other, so as to reduce the mutual interference of the rotation movements. Thereby, the rotation movements can be maximally superimposed. Therefore, a better rotation effect can be achieved and more position changes can be realized. In connection with the rotation movement of the first support seat 312 on the first component, more position changes can be achieved.

As described above, in the embodiments of the present disclosure, the floating mechanism 300 may include one or more connection rod assemblies as described above. In these embodiments, the respective first support seats of the connection rod assemblies may be separate elements, or may be formed as a same single element. The respective second support seat of the connection rod assemblies may be separate elements, or may be formed as a same single element.

In the embodiments, the connection positions of the first support seats with the first components of the connection rod assemblies may be separated by a predetermined distance, or may be substantially at the same position. The connection positions of the second support seats with the second components of the connection rod assemblies may be separated by a predetermined distance, or may be substantially at the same position.

For example, in some embodiments, the floating mechanism 300 may include a first connection rod assembly and a second connection rod assembly. Each connection rod assembly may have the same structure as the connection rod assembly described in the embodiments above, which will not be described again here.

Figure 22:
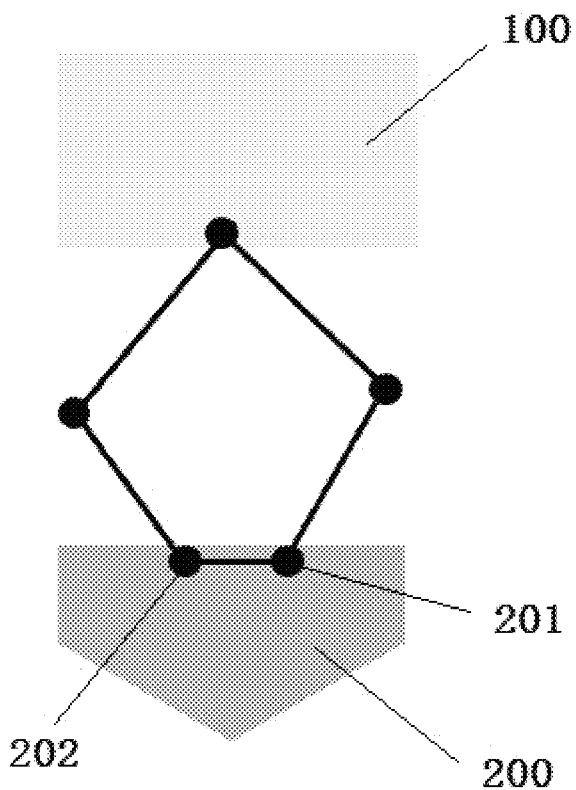
FIG. 22 schematically shows the floating mechanism in one embodiment.

Referring to FIG. 22, the second support seat of the first connection rod assembly and the second support seat of the second connection rod assembly may be separate elements. The second support seat of the first connection rod assembly may be connected to the second component 200 at a first connection location 201, the second support seat of the second connection rod assembly may be connected to the second component 200 at a second connection location 202, and the first connection location 201 and the second connection location 202 may be separated by a predetermined distance. That is, the second support seat of the first connection rod assembly and the second support seat of the second connection rod assembly may be connected to the second component 200 at a predetermined distance.

In the embodiments above, the third rotation axis of the first connection rod assembly may be parallel to the third rotation axis of the second connection rod assembly. In this way, the rotations of the second connection seats of the two connection rod assemblies relative to the first connection seat through the third rotation pair may be parallel to each other or in a same plane, thereby reducing the mutual interference of the two rotation movements and improving the overall maneuverability of the motion system composed of the two connection rod assemblies and the first and second components.

In the embodiments above, the sixth rotation axis of the first connection rod assembly may be parallel to the sixth rotation axis of the second connection rod assembly. In this way, the rotations of the first connection seats of the two connection rod assemblies relative to the first component through the sixth rotation pair may be parallel to each other or in a same plane, thereby reducing the mutual interference of the two rotation movements and improving the overall maneuverability of the motion system composed of the two connection rod assemblies and the first and second components.

In the embodiments above, the seventh rotation axis of the first connection rod assembly may be parallel to the seventh rotation axis of the second connection rod assembly. In this way, the rotations of the second connection seats of the two connection rod assemblies relative to the second component through the seventh rotation pair may be parallel to each other or in a same plane, thereby reducing the mutual interference of the two rotation movements and improving the overall maneuverability of the motion system composed of the two connection rod assemblies and the first and second components.

Referring to FIG. 22, compared with the embodiment in which the floating mechanism includes only one connection rod assembly, in these embodiments, the second support seat of the first connection rod assembly and the second support seat of the second connection rod assembly may be connected to the second component with a predetermined distance between the connection locations thereof. Therefore, the first connection rod assembly, the second connection rod assembly and the second component may form a closed system (as shown by the pentagon in FIG. 22) and the second component itself may be one link in the system (for example, as shown in FIG. 22, the control panel 200 (as an example of the second component) is one side of the pentagon that represents the closed system) while the other links in the closed system (e.g., the other five sides of the pentagon in FIG. 22) may be coupled structures, that is, their motions may affect each other. Therefore, when the operating the second component to move relative to the first component, the directivity of the motion will be consistent with the operating direction, and the operating performance will be better.

Similarly, the first support seat of the first connection rod assembly and the first support seat of the second connection rod assembly may also be separate elements and be connected to the main body 100 (as an example of the first component) with a predetermined distance between the connection locations thereof, thereby enjoying the similar advantages as described above.

Further, referring to FIGS. 1-4, in one embodiment, the floating mechanism 300 may include a first rising-and-lowering mechanism 310 and a second rising-and-lowering mechanism 320. The first rising-and-lowering mechanism 310 may be mounted on the first component, and may have a structure which enables one end of the first rising-and-lowering mechanism 310 to rise and fall relative to the first component in a vertical direction. This structure can enable at least one end of the first rising-and-lowering mechanism 310 to rise and fall relative to the first component in a vertical plane.

The second rising-and-lowering mechanism 320 may be used to support the second component. One end of the second rising-and-lowering mechanism 320 may be rotatably connected to the first rising-and-lowering mechanism 310, and the other end of the second rising-and-lowering mechanism 320 may rise and fall relative to the first rising-and-lowering mechanism 310 in a vertical direction.

The structures of the first rising-and-lowering mechanism 310 and the second rising-and-lowering mechanism 320 for achieving the rising and falling may be the same or different.

Furthermore, since the second rising-and-lowering mechanism 320 may be rotatably connected to the first rising-and-lowering mechanism 310, the second rising-and-lowering mechanism 320 may be rotated relative to the first rising-and-lowering mechanism 310 in a plane perpendicular to the center line of rotation of them. In connection with the rising and falling movements in the vertical direction, the floating mechanism 300 can achieve the movements in more directions.

In addition, the first rising-and-lowering mechanism 310 and the second rising-and-lowering mechanism 320 each have an independent rising function. Therefore, the position change of the floating mechanism 300 may be more flexible. On the other hand, in the floating mechanism 300, the rising-and-lowering mechanism and the rotation structure are designed to be moved in a linkage. Therefore, it will have good linkage, quick response, small space and large operating range.

Referring to FIGS. 1-4, in one embodiment, two first rising-and-lowering mechanisms 310 and two second rising-and-lowering mechanisms 320 may be provided. One first rising-and-lowering mechanism 310 may be rotatably connected with one second rising-and-lowering mechanism 320 to form one connection rod assembly. The connection ends of the two first rising-and-lowering mechanisms 310 in the two connection rod assemblies to be connected with the second rising-and-lowering mechanisms 320 may be arranged as being close to or away from each other.

The two first rising-and-lowering mechanisms 310 may be connected to the main body 100, and the two second rising-and-lowering mechanisms 320 may be used to support the control panel 200.

In other embodiments, the floating mechanism 300 may include only one connection rod assembly, that is, one first rising-and-lowering mechanism 310 and one second rising-and-lowering mechanism 320, to achieve the floating function. Alternatively, the floating mechanism 300 may include more than two first connection arms and one second connection arm to achieve the floating function so as to further ensure the stability and balance of the connection and support between the first component and the second component. The number of the connection rod assembly may be determined according to actual needs based on the present disclosure. When multiple floating mechanisms 300 are provided between the first component and the second component, these floating mechanisms 300 may be separated from each other or independent, or may be shared or partially shared.

In some embodiments, in order to achieve the rising and falling function, the first rising-and-lowering mechanism 310 and the second rising-and-lowering mechanism 320 may be designed as a four-bar structure, such as a parallelogram structure or other four-bar structure.

Figure 5:
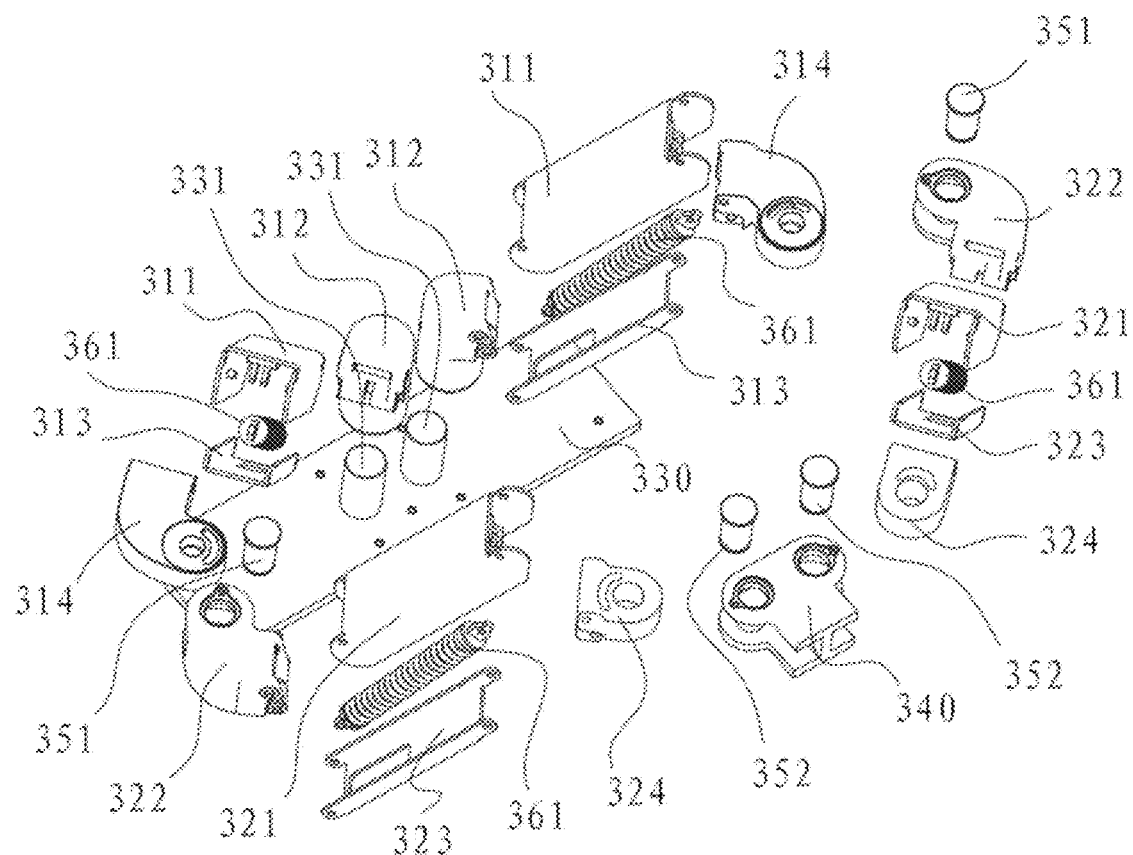
FIG. 5 is an exploded view of the embodiment shown in FIG. 4.
Figure 6:
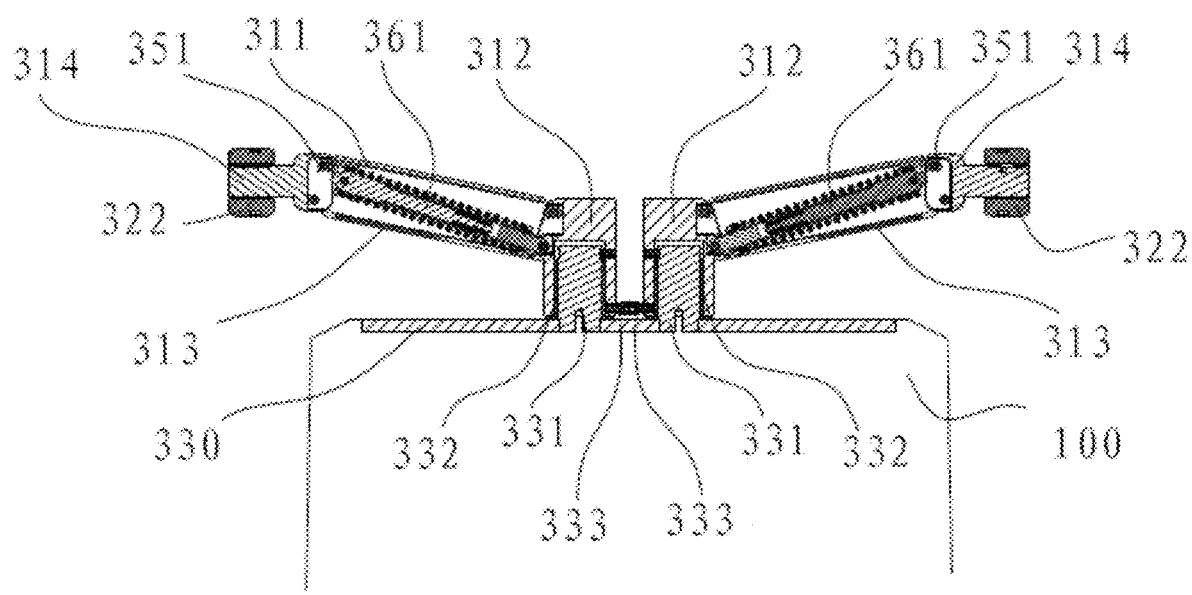
FIG. 6 is a sectional view of the first rising-and-lowering mechanism and the main body in one embodiment.

In one embodiment, an exemplary structure of the first rising-and-lowering mechanism 310 and the second rising-and-lowering mechanism 320 is disclosed. Referring to FIGS. 4-6, the first rising-and-lowering mechanism 310 may include a first upper bracket 311, a first support seat 312, a first lower bracket 313 and a first connection seat 314. The first upper bracket 311, the first support seat 312, the first lower bracket 313 and the first connection seat 314 may be sequentially rotatably connected end to end to form a parallelogram structure (or other four-bar structure). The second rising-and-lowering mechanism 320 may be rotatably connected to the first connection base 314.

Specifically, the ends of the first upper bracket 311 may be respectively rotatably connected to the first support seat 312 and the first connection seat 314 through respective shafts. The ends of the first lower bracket 313 may be respectively rotatably connected to the first support seat 312 and the first connection seat 314 through respective shafts. The first upper bracket 311 and the first lower bracket 313 may be parallel to each other, thereby forming a parallelogram structure in one plane, in which the four rotation pairs are respectively located at the four vertices of the parallelogram. Therefore, the first connection seat 314 may be able to rise and fall relative to the first support seat 312 through the first upper bracket 311 and the first lower bracket 313.

Referring to FIGS. 4-6, in one embodiment, the second rising-and-lowering mechanism 320 may have similar structure to the first rising-and-lowering mechanism 310. Specifically, the second rising-and-lowering mechanism 320 may include a second upper bracket 321, a second connection seat 322, a second lower bracket 323 and a second support seat 324. The second upper bracket 321, the second connection seat 322, the second lower bracket 323 and the second support seat 324 may be sequentially rotatably connected end to end to form a parallelogram structure (or other four-bar structure). The second connection base 322 may be rotatably connected to the first connection seat 324 of the first rising-and-lowering mechanism 310.

Specifically, the ends of the second upper bracket 321 may be respectively rotatably connected to the second connection seat 322 and the second support seat 324 through respective shafts. The ends of the second lower bracket 323 may be respectively rotatably connected to the second connection seat 322 and the second support seat 324 through respective shafts. The second upper bracket 321 and the second lower bracket 323 may be parallel to each other, thereby forming a parallelogram structure in one plane, in which the four rotation pairs are respectively located at the four vertices of the parallelogram. Therefore, the second support seat 324 may be able to rise and fall relative to the second connection seat 322 through the second upper bracket 321 and the second lower bracket 323. The second connection seat 322 may be mounted on the first connection seat 314 such that the rising and falling of the first connection seat 314 can bring the entire second rising-and-lowering mechanism 320 to rise and fall.

In the parallelogram structure above, the balance thereof at a certain position may be achieved by increasing the frictional force at the rotation pair so as to stop the floating mechanism 300 at the desired position. In some embodiments, in order to further improve the stability of the parallelogram structure, a damping balance compensation system may also be provided.

Figure 7:
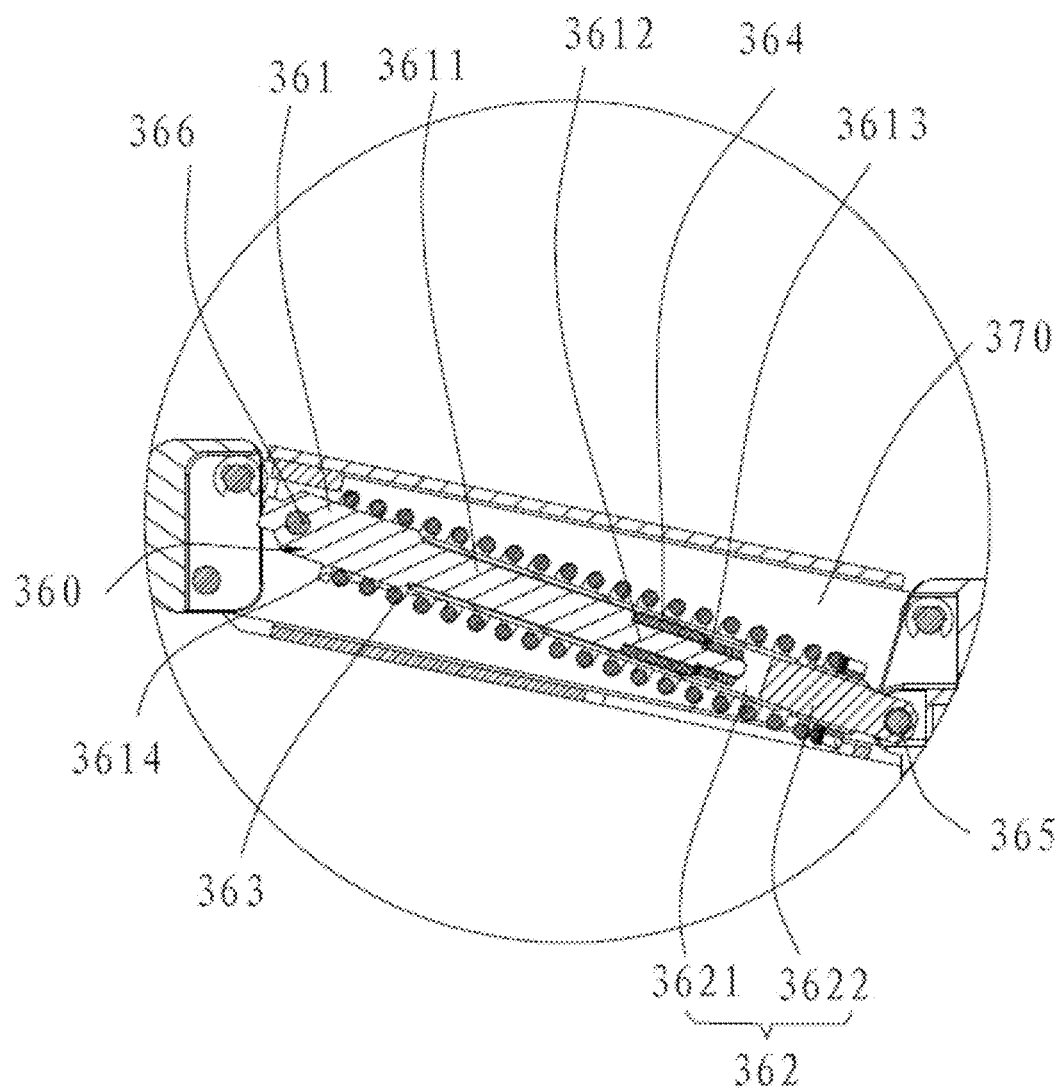
FIG. 7 is a sectional view of the damping balance compensation system in one embodiment.

Referring to FIG. 7, the damping balance compensation system 360 may be disposed in the receiving space 370 of the four-bar structure formed by the first rising-and-lowering mechanism 310 and/or the second rising-and-lowering mechanism 320, and be used to compensate for the change of the torque acting on the first rising-and-lowering mechanism 310 due to the rotation of the first rising-and-lowering mechanism 310 by a certain angle, so as to keep the torque acting on the first rising-and-lowering mechanism 310 in balance, thereby smoothly supporting the control panel 200 and the display 400.

Referring to FIG. 6 and FIG. 7, the damping balance compensation system 360 may be received in the receiving space 370, and may include a guide rod 361, a guide cylinder 362 and a spring 363. The guide cylinder 362 may include an open end 3621 and a first connection end 3622.

The first connection end 3622 may be connected to the first support seat 312 through a shaft 365. The open end 3621 may be recessed inward to form a receiving space 370. The guide rod 361 may include a second connection end 3611, a first extension end 3612 and a second extension end 3613. The second connection end 3611 may be rotatably connected to the first upper bracket 311 through a shaft 366, and the end of the second connection end 3611 away from the first connection seat 314 may protrude to form the first extension end 3612. The end of the first extension end 3612 away from the second connection end 3611 may protrude to form the second extension end 3613. The sizes of the second connection end 3611, the first extension end 3612 and the second extension end 3613 may be sequentially reduced, such that the guide rod 361 may be formed in a three-step shape.

The second extension end 3613 may be inserted into the receiving space 370 of the guide cylinder 362 through the open end 3621, and be able to be moved in the axial direction relative to the guide cylinder 362 in the receiving space 370. A friction pad 364 that abuts against the inner surface of the receiving space 370 may be sleeved on the second extension end 3613. One end of the friction pad 364 may abut the connection between the second extension end 3613 and the first extension end 3612, and the other end may be fixed to the end of the second extension end 3613 away from the first extension end 3612 by a fixing nut so as to prevent it from falling off.

The spring 363 may be sleeved outside the guide rod 361 and the guide cylinder 362, and the guide rod 361 and the guide cylinder 362 may pass through the middle of the spring 363 in the axial direction. Specifically, the second connection end 3611 of the guide rod 361 may be provided with a flange 3614, and the first connection end 3622 of the guide cylinder 362 may be provided with a spring adjustment nut. The spring 363 may abut between the flange 3614 and the spring adjustment nut. The spring 363 may generate a thrust force to the guide rod 361, and the user can adjust the magnitude of the thrust force generated by the spring 363 to the guide rod 361 by adjusting the distance between the spring adjustment nut and the flange 3614. The thrust force generated by the spring 363 can balance the first rising-and-lowering mechanism 310 (or the second rising-and-lowering mechanism 320).

In operation, the floating mechanism 300 of the ultrasound diagnostic apparatus may need to be rotated so as to make the control panel 200 to be moved upward or downward by a certain angle. In some cases, after the floating mechanism 300 is rotated to a new position, the length of the spring 363 will change, that is, the amount of compression of the spring 363 will change. In this case, the first upper bracket 311 may not be able to stably support the control panel 200 and the display 400 in the desired position.

With the structure of the present embodiment, such torque change can be compensated. As shown in FIG. 7, in the present embodiment, a friction pad 364 may be sleeved on the second extension end 3613 of the guide rod 361. The friction pad 364 may be abutted against the inner surface of the receiving space 370 of the guide cylinder 362. When in the new position, the first upper bracket 311 will have a tendency to rotate downward. The tendency to move downward of the first upper bracket 311 will cause a tendency of the guide rod 361 to move along the axial direction toward the guide cylinder 362, that is, a tendency of the guide rod 361 to move deeply into the guide cylinder 362. In this case, since the friction pad 364 sleeved on the second extension end 3613 of the guide rod 361 is abutted against the inner surface of the guide cylinder 362, a static friction force may be generated between the friction pad 364 and the inner surface of the guide cylinder 362. Since the guide rod 361 is connected to the first upper bracket 311, this static frictional force will act on the first upper bracket 311. In this way, the torque of the frictional force can make the torques acting on the first upper bracket 311 to be balanced, thereby enabling the floating 300 to stay in the desired position.

In the present embodiment, the force generated by the spring 363 may be used to balance the torques acting on the first upper bracket 311, and the static friction force between the friction pad 364 arranged on the guide rod 361 and the inner surface of the guide cylinder 362 may be used to further compensate and balance the torques acting on the first upper bracket 311. Therefore, the first upper bracket 311 can be balanced at any position. Furthermore, when the spring force is attenuated, the attenuation of the spring force can be compensated, so that the first upper bracket 311 can still keep be balanced, thereby providing stable support for the control panel 200 and the display 400. It can be understood that, in other embodiments, the damping compensation system 360 may also be implemented in other manners, which will not be limited herein. For example, gas spring, tension spring, torsion spring and other structures may be used.

The exemplary structure of the first rising-and-lowering mechanism 310 and the second rising-and-lowering mechanism 320 is described above. However, the first rising-and-lowering mechanism 310 and the second rising-and-lowering mechanism 320 may also be implemented with different rising-and-lowering mechanisms. The rising-and-lowering mechanism that achieves the rising and falling movements of the first rising-and-lowering mechanism 310 and the second rising-and-lowering mechanism 320 may also be implemented with other structures that can achieve the rising and falling functions, such as a structure driven by a motor.

In the floating mechanism 300, the rising and falling movement of the second support seat 324 is a synthesis of the rising and falling movements of the first rising-and-lowering mechanism 310 and the second rising-and-lowering mechanism 320, therefore the moving trajectory thereof is more variable. Furthermore, the second connection seat 322 and the first connection seat 314 are rotatably connected. Therefore, the first rising-and-lowering mechanism 310 is able to be rotated relative to the second rising-and-lowering mechanism 320. This rotation, in connection with the rising and falling movement, can enable the second component mounted on the second support seat 324 to have more changes of orientation relative to the first component mounted on the first support seat 312.

The rotatable connection between the first rising-and-lowering mechanism 310 and the second rising-and-lowering mechanism 320 may be achieved by forming the rotation pair. The rotation pair (including other rotation pairs in the embodiments) may be any suitable rotation pair mechanism, such as the rotation pair formed by a limiting pin and a pin hole or the rotation pair formed by a rotation seat and a rotation shaft, and so on. Examples of some rotation pairs will be described in detail below with reference to the drawings. However, it will be understood that the structure of the rotation pair mentioned above will not be limited to the examples described in detail below.

Figure 8:
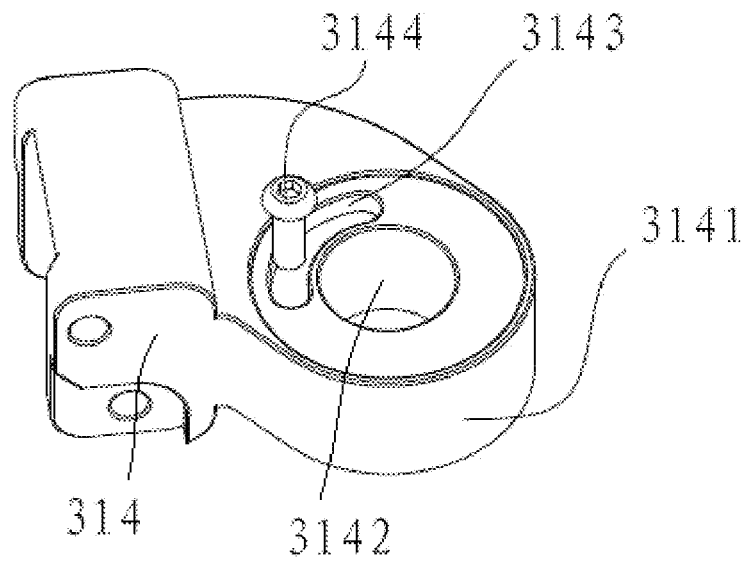
FIG. 8 is a schematic diagram of the limiting structure in the mounting seat in one embodiment.

Referring to FIGS. 5, 6 and 8, in one embodiment, one end of the first connection seat 314 may be provided with a first lug 3141. The first lug 3141 may be formed by a side edge of the first connection seat 314 facing away from the first upper bracket 311 and the first lower bracket 313, and be provided with a first shaft hole 3142 which may be rotatably connected with the corresponding second rising-and-lowering mechanism 320. The second rising-and-lowering mechanism 320 may be installed at the first shaft hole 3142, and be connected to the first shaft hole 3142 by a first rotation shaft 351.

Figure 16A:
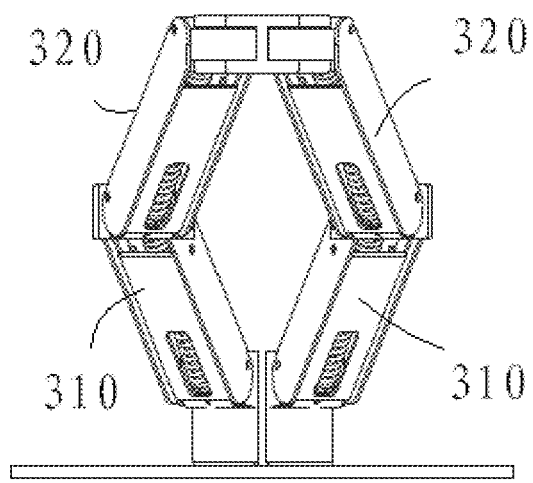
Figure 16B:
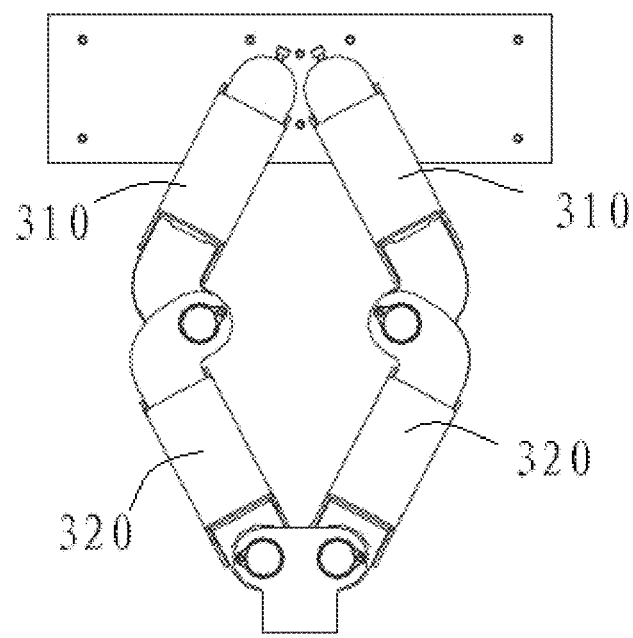

Referring to FIG. 4, in one embodiment, the two first lugs 3141 on the two first connection seats 314 may be bent inwardly toward each other, such that the connection lines between the two mounting seats 330, the two connection rod assemblies and the fixation seat 340 form a hexagon. The hexagon herein may include not only hexagons that are generally known and in a same plane, but also hexagons within a spatial range of which the sides are in different planes, such as shown in FIGS. 16a and 16b. In some embodiments, the two first lugs 3141 may also be formed by bending outwardly away from each other, which will not be limited herein.

In order to limit the relative rotation angle between the first connection seat 314 and the second connection seat 322, at least one of the first connection seat 314 and the second connection seat 322 may be provided with a first limiting groove that may be arranged in an arc around the rotation center line between the first connection seat 314 and the second connection seat 322, while the other of the first connection seat 314 and the second connection seat 322 may be provided with a first limiting pin which may cooperate with the first limiting groove so as to limit the relative rotation angle between the first connection seat 314 and the second connection seat 322. That is, in the case that the first limiting groove is arranged in the first connection seat 314, the first limiting pin is arranged in the second connection seat 322; in the case that the first limiting groove is arranged in the second connection seat 322, the first limiting pin is arranged in the first connection seat 314; in the case that both the first connection seat 314 and the second connection seat 322 are provided with the first limiting grooves, the first limiting pins are arranged in both the first connection seat 314 and the second connection seat 322 so as to cooperate with the first limiting grooves.

Specifically, referring to FIG. 8, in one embodiment, the first lug 3141 may be provided with the arc-shaped first limiting groove 3143. The first limiting groove 3143 may surround the first shaft hole 3142 in the circumferential direction, that is, may be disposed around the rotation center line between the first connection seat 314 and the second connection seat 322, so as to limit the rotation angle of the second rising-and-lowering mechanism 320 with respect to the first rising-and-lowering mechanism 310. Referring to FIGS. 5 and 8, when they are assembled, the second connection seat 322 of the second rising-and-lowering mechanism 320 may be installed at the first shaft hole 3142 of the first rising-and-lowering mechanism 310 through the first rotation shaft 351, while the first limiting pin 3144 may be fixedly connected with the second connection seat 322. In addition, one end of the first limiting pin 3144 may be inserted into the first limiting groove 3143 and be limited to move in the first limiting groove 3143, thereby limiting the rotation angle of the second connection seat 322.

The floating mechanism 300 may include a mounting seat 330. The mounting seat 330 may be installed on a base that needs to use the floating mechanism 300. In the present embodiment, the base may be the main body 100 of the ultrasound diagnostic apparatus. In other embodiments, the base may also be various platforms or other supporting or connecting structures that need to use the floating mechanism 300.

In order to enable the floating mechanism 300 to achieve the movement in more directions, in one embodiment, the first rising-and-lowering mechanism 310 may be rotatably connected to the mounting seat 330, such that the first rising-and-lowering mechanism 310 and the second rising-and-lowering mechanism 320 can be in whole rotated with respect to the mounting seat 330, thereby achieving more movements in connection with the movements mentioned above.

The end of the first rising-and-lowering mechanism 310 away from the second rising-and-lowering mechanism 320 may be rotatably connected to the mounting seat 330 through a rotation pair. The second rising-and-lowering mechanism 320 may be rotatably connected to the end of the first rising-and-lowering mechanism 310 away from the mounting seat 330 through a rotation pair.

In one embodiment, the rotation center line of the first rising-and-lowering mechanism 310 relative to the mounting seat 330 may be consistent with the direction of the rising and falling movement of the first rising-and-lowering mechanism 310, such that the first rising-and-lowering mechanism 310 can be translated in a plane perpendicular to the rotation center line of the mounting seat 330. This plane may usually be a horizontal plane.

In other embodiments, the rotation center line of the first rising-and-lowering mechanism 310 relative to the mounting seat 330 may be at an angle with respect to the direction of the rising and falling movement of the first rising-and-lowering mechanism 310, such that the first rising-and-lowering mechanism 310 can be rotated in a plane which is at an angle with respect to the direction of the rising and falling movement.

Referring to FIG. 6, in one embodiment, one end of the first rising-and-lowering mechanism 310 may be rotatably connected to the mounting seat 330 through a rotation pair, and can be rotated taking the connection between the first rising-and-lowering mechanism 310 and the mounting seat 330 as an axis. The second rising-and-lowering mechanism 320 may be rotatably connected to the first rising-and-lowering mechanism 310 such that the mounting seat 330 can bring the first rising-and-lowering mechanism 310 and thereby bring the second rising-and-lowering mechanism 320 to rotate in the defined plane taking the mounting seat 330 as the fulcrum.

In the case where the desired number of the degrees of freedom of the floating mechanism 300 is relatively small, the first rising-and-lowering mechanism 310 may be fixedly connected to the mounting seat 330, or the first rising-and-lowering mechanism 310 may be directly fixed on the first component.

Further, in one embodiment, in order to implement the rotatable connection between the mounting seat 330 and the first rising-and-lowering mechanism 310, at least one of the mounting seat 330 and the first support seat 312 may be provided with a second shaft hole, while the other one of the mounting seat 330 and the first support seat 312 may be provided with a second rotation shaft that cooperates with the second shaft hole such that the first support seat 312 can rotate with respect to the mounting seat 330. That is, in the case that the mounting seat 330 is provided with the second shaft hole, the second rotation shaft 331 may be provided in the first support seat 312; in the case that the first support seat 312 is provided with the second shaft hole, the second rotation shaft 331 may be provided in the first connection seat 314; in the case that the first connection seat 314 and the second connection seat 322 are both provided with the second shaft hole, the first connection seat 314 and the first support seat 312 may both be provided with the second rotation shaft 331 that cooperates with the second shaft hole.

Specifically, referring to FIG. 6, the second rotation shaft 331 may be provided in the mounting seat 330, the second shaft hole (not shown in the figure) may be provided in the first support seat 312, and the first support seat 312 may be arranged on the second rotation shaft 331 upside down. The second rotation shaft 331 may be generally cylindrical, and be fixedly mounted on the main body 100. The first support seat 312 may be generally a hollow cylinder with one end open, and the second shaft hole may be located in the middle of the cylinder and be rotatably sleeved on the second rotation shaft 331 through the open end. In this way, the second rotation shaft 331 and the first support seat 312 form a rotation pair.

In one embodiment, in order to limit the rotation angle of the first support seat 312 relative to the mounting seat 330, at least one of the mounting seat 330 and the first support seat 312 may be provided with a second limiting groove that is arranged in an arc around the rotation center line between the mounting seat 330 and the first support seat 312, and the other one of the mounting seat 330 and the first support seat 312 may be provided with a second limiting pin. The second limiting pin may cooperate with the second limiting groove to limit the relative rotation angle between the mounting seat 330 and the first support 312. That is, in the case that the mounting seat 330 is provided with the second limiting groove, the second limiting pin may be arranged in the first support seat 312; in the case that the first support seat 312 is provided with the second limiting groove, the second limiting pin may be arranged in the first connection seat 314; and in the case that the first connection seat 314 and the second connection seat 322 are both provided with the second limiting groove, the first connection seat 314 and the first support seat 312 may be both provided with the second limiting pin that cooperates with the second limiting groove.

Figure 9:
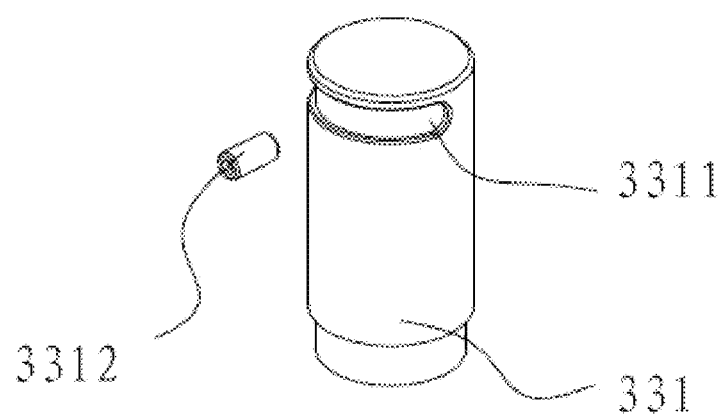
FIG. 9 is a sectional view of the second rising-and-lowering mechanism and the fixation seat in one embodiment.

Referring to FIG. 9, in one embodiment, the second limiting groove 3311 may be provided on the surface of the second rotation shaft 331, and the second limiting pin 3312 may pass through the wall of the second shaft hole and be inserted into the second limiting groove 3311 so as to limit the rotation angle of the first support seat 312 relative to the second rotation shaft 331.

In one embodiment, the mounting seat 330 may be mounted on the top of the main body 100, and the two first rising-and-lowering mechanisms 310 may be respectively rotatably mounted on opposite sides of the mounting seat 330. The rotating structure of the mounting seat 330 may be designed according to needs, as long as function of driving the first rising-and-lowering mechanism 310 and the second rising-and-lowering mechanism 320 in the corresponding connection rod assembly to rotate in a plane relative to the main body under the action of external force can be achieved. For example, the second rotation shaft 331 may be rotatably mounted on the main body 100, and the first support seat 312 may be sleeved on the second rotation shaft 331 so as to rotate with the second rotation shaft 331 relative to the main body 100. Alternatively, the second rotation shaft 331 and the first support seat 312 may be designed as an integral rotating element, which may be directly rotatably mounted on the main body 100.

Referring to FIG. 6, in one embodiment, the mounting seat 330 may further include a bushing 332 disposed between the second rotation shaft 331 and the first support seat 312. The bushing 332 may be used to reduce the wear of the second rotation shaft 331 and the first support 312. The mounting seat 330 may further include a damping pin 333 that passes through the first support seat 312 and is tightened and abuts on the bushing 332 for adjusting the rotation damping force between the second rotation shaft 331 and the first support seat 312.

When supporting the second component, the second rising-and-lowering mechanism 320 may be fixedly connected to the second component, which may be generally used in an environment that requires less floating orientation. Alternatively, the second rising-and-lowering mechanism 320 may be rotatably connected with the second component, which will increase the movable orientations of the entire floating mechanism 300.

The connection between the second rising-and-lowering mechanism 320 and the second component may be implemented in many suitable ways. It may be a fixed connection or a rotatable connection. The second rising-and-lowering mechanism 320 may be directly fixedly or rotatably connected to the second component. Alternatively, the second rising-and-lowering mechanism 320 may be fixedly or rotatably connected to the second component via an intermediate element.

In one embodiment, a fixation seat for connecting the second component may further be provided. The second rising-and-lowering mechanism 320 (e.g., the second connection arm) may be rotatably connected to the fixation seat, so as to enable the second component to be rotated relative to the second rising-and-lowering mechanism 320.

In one embodiment, in order to achieve the rotation, at least one of the second connection arm and the fixation seat may be provided with a third rotation shaft, and the other one may be provided with a third shaft hole, so as to realize the rotation connection of the shaft hole.

Figure 10:
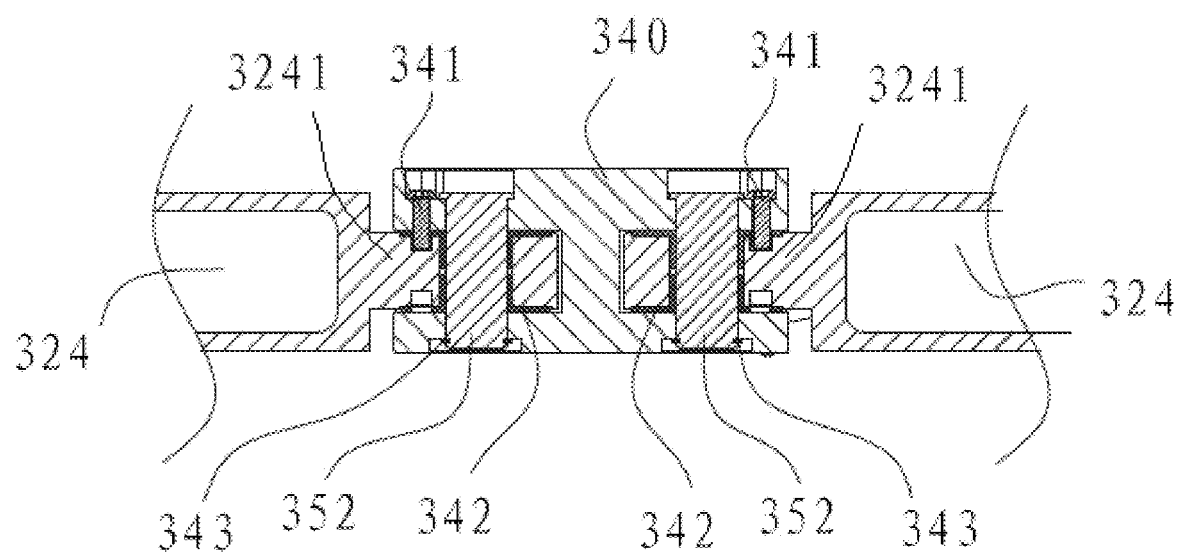
FIG. 10-FIG. 18 schematically show the floating structure in various states, where a and b represent schematic diagrams in different angles in the same state.

Referring to FIG. 10, in one embodiment, the third shaft hole (not shown in the figure) may be arranged in the second support seat 324, and the fixation seat 340 may be installed on the third shaft hole through the third rotation shaft 352. Specifically, the second support seat 324 may be provided with a protruding second lug 3241, and the third shaft hole (not shown in the figure) for rotatably connecting with the fixation seat 340 may be formed in the second lug 3241. The fixation seat 340 may be installed on the third shaft hole through the third rotation shaft 352.

In addition, in one embodiment, in order to limit the rotation angle of one of the second support seat 324 and the fixation seat 340 relative to the other, at least one of the second support seat 324 and the fixation seat 340 may be provided with a third limiting groove (not shown in the figure) that is arranged in an arc around the rotation center line between the second support seat 324 and the fixation seat 340, and the other may be provided with a third limiting pin 341 that cooperates with the third limiting groove to limit the relative rotation angle of the second support seat 324 and the fixation seat 340.

Specifically, the third limiting groove may be arranged on the periphery of the third shaft hole, and the third limiting pin 341 may be fixedly installed on the fixation seat 340.

Generally, the rotation center line of the second rising-and-lowering mechanism 320 relative to the fixation seat 340 may be consistent with the lifting movement direction (i.e., the vertical direction) of the second rising-and-lowering mechanism 320, so that the fixation seat 340 and the second component thereon can be rotated in the horizontal plane. In other embodiments, the rotation center line of the second rising-and-lowering mechanism 320 relative to the fixation seat 340 may be at a certain angle with the lifting movement direction (i.e., the vertical direction) of the second rising-and-lowering mechanism 320.

In addition, in one embodiment, the rotation center line of the second rising-and-lowering mechanism 320 relative to the fixation seat 340 may be consistent with (parallel to or coincident with) the rotation center line of the first rising-and-lowering mechanism 310 relative to the mounting seat 330, such that the first component and the second component may be in the same horizontal plane. Furthermore, the rotation center line of the second rising-and-lowering mechanism 320 relative to the first rising-and-lowering mechanism 310 may be consistent with (parallel to or coincident with) the rotation center lines above, such that the rotation movement of the floating mechanism 300 is more consistent with people's usual operating habits.

In addition, in one embodiment, the lifting movement direction of the first rising-and-lowering mechanism 310 may be consistent with (parallel to or coincident with) the rotation center line of the second rising-and-lowering mechanism 320 relative to the first rising-and-lowering mechanism 310, such that the rotation movement of the floating mechanism 300 is more consistent with people's usual operating habits.

Referring to FIGS. 1-4, in one embodiment, one mounting seat 330 is installed on the top of the main body 100. There may be two first rising-and-lowering mechanisms 310 and two second rising-and-lowering mechanisms 320. One first rising-and-lowering mechanism 310 may be rotatably connected at a predetermined angle with one second rising-and-lowering mechanism 320 to form one connection rod assembly. The two first rising-and-lowering mechanisms 310 in the two connection rod assemblies may be respectively rotatably connected to the two second rotation shafts 331 in the mounting seat 330, and the two second rising-and-lowering mechanisms 320 may be rotatably connected to both sides of the fixation seat 340. The control panel 200 (or the display 400 or other components requiring floating support) may be fixedly mounted on the fixation seat 340, and can achieve the full-floating operation with the two connection rod assemblies relative the main body 100, in which the control panel 200 is able to lift with the two connection rod assemblies in the vertical plane where the rotation center line of the first rising-and-lowering mechanism 310 relative to the mounting seat 330 is located, and able to translate in the front, back, left and right direction and rotate in the translation plane.

In the embodiment, the first rising-and-lowering mechanism 310 and the second rising-and-lowering mechanism 320 may be any suitable supporting or connection arm. For example, they may be elements formed by a single rod, or may be formed by multiple components (e.g., those shown in FIG. 5). The first rising-and-lowering mechanism 310 and the second rising-and-lowering mechanism 320 may be any suitable shapes, such as linear, curved or other shapes.

Referring to FIGS. 11-18, different states of the floating mechanism 300 are shown, where the view marked with a is the front view in a normal use state and the view marked with b is the top view in the normal use state.

Figure 11A:
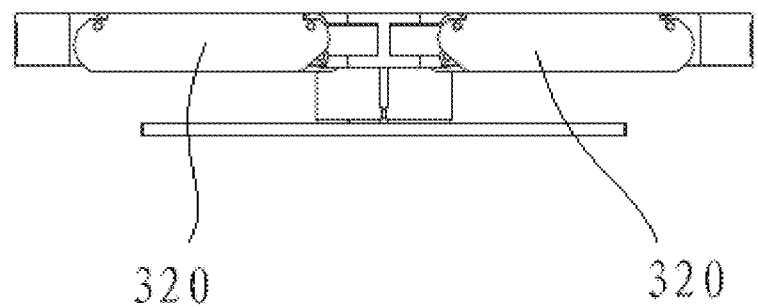
Figure 11B:
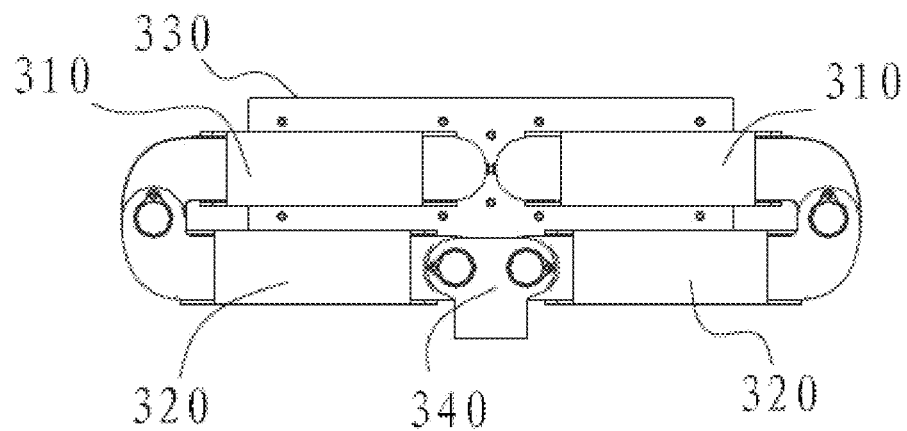
Figure 12A:
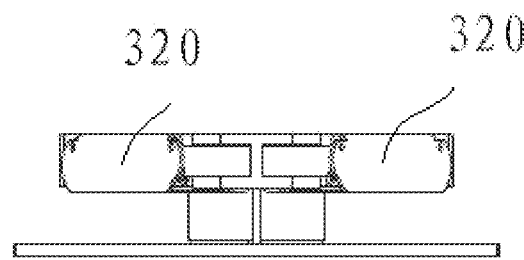
Figure 12B:
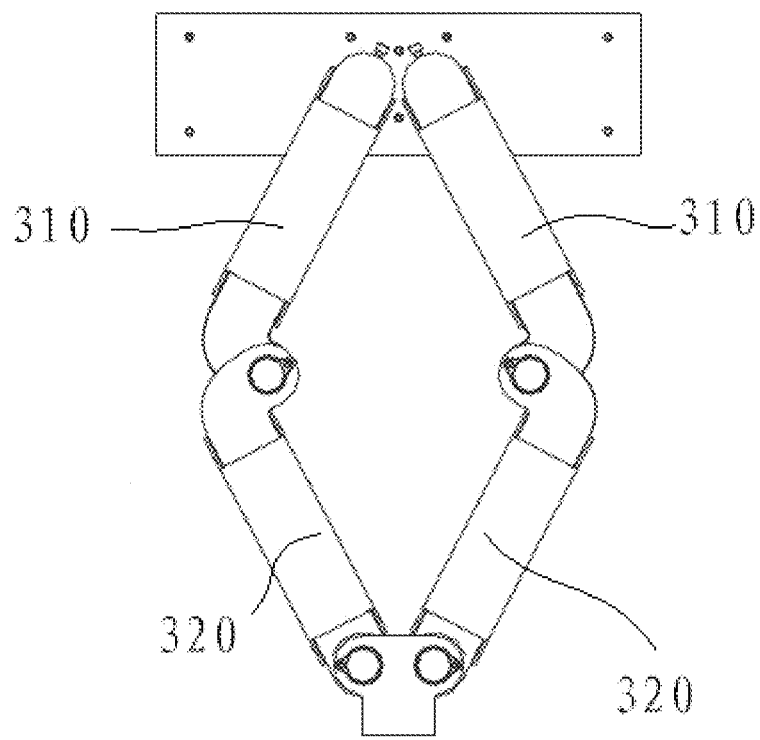
Figure 13A:
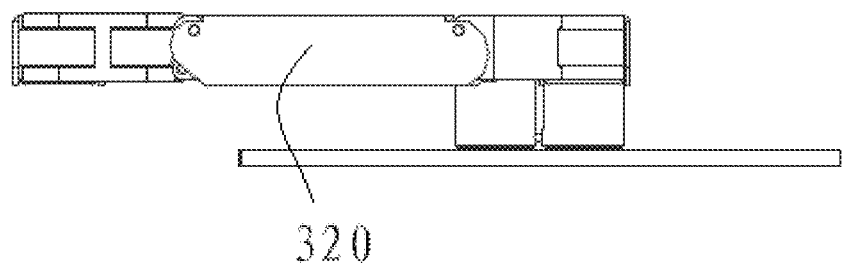
Figure 13B:
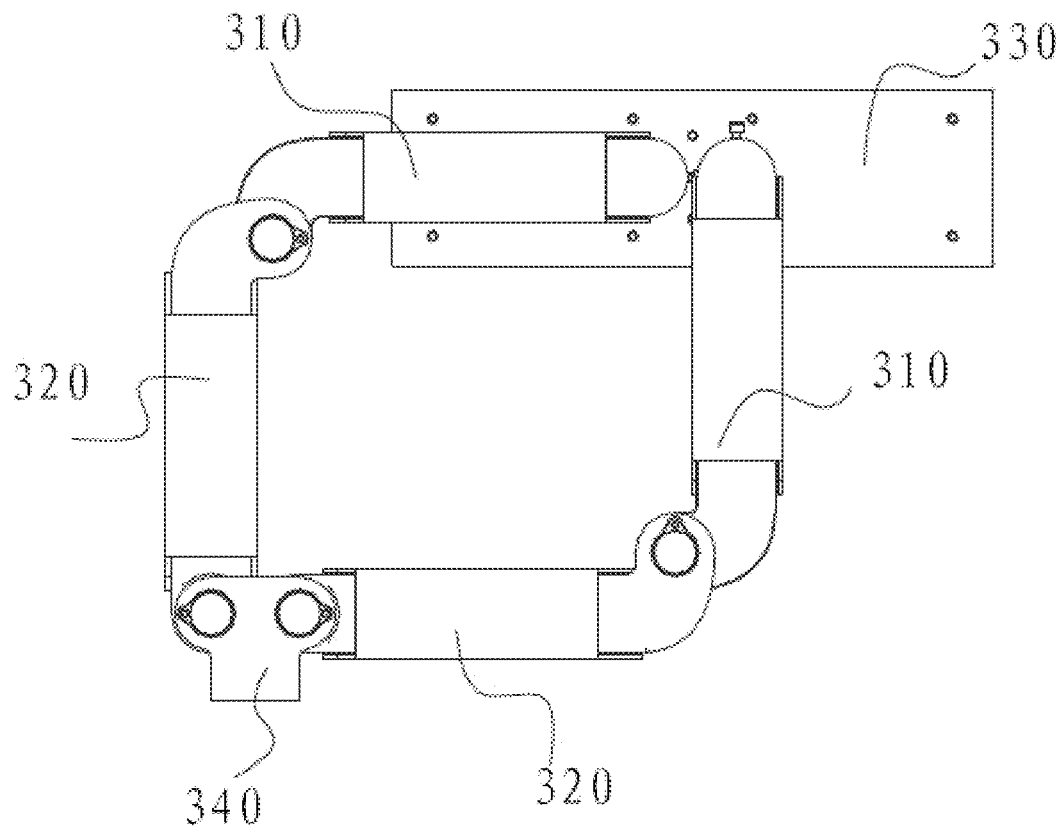
Figure 14A:
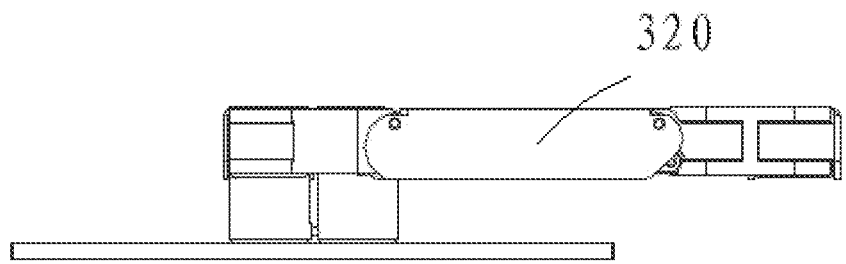
Figure 14B:
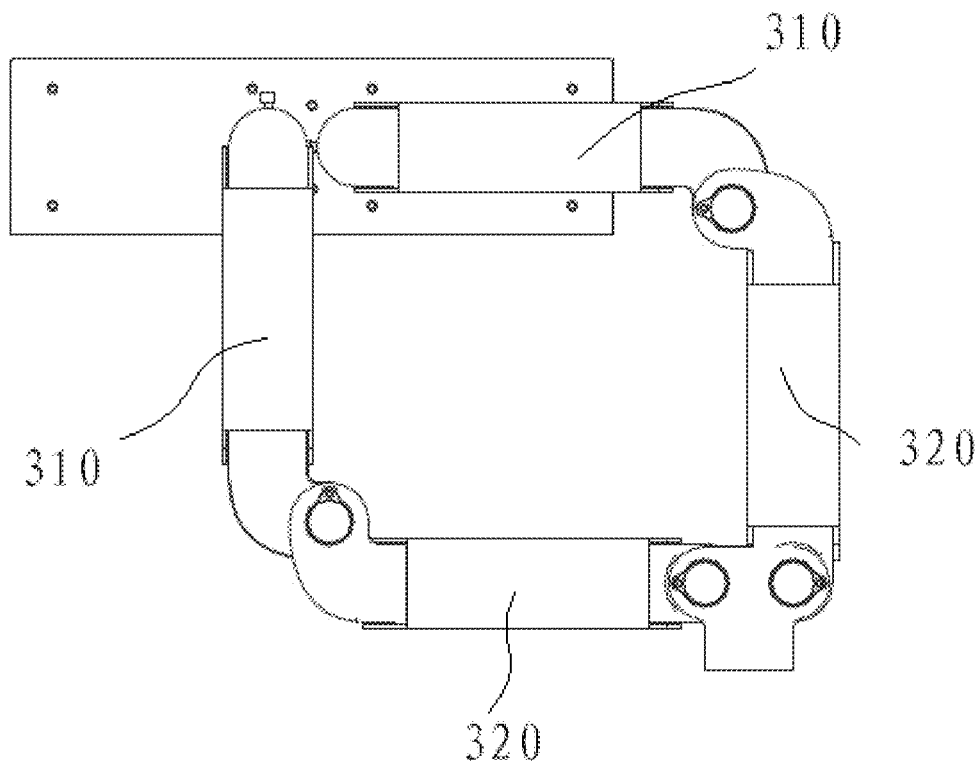
Figure 15A:
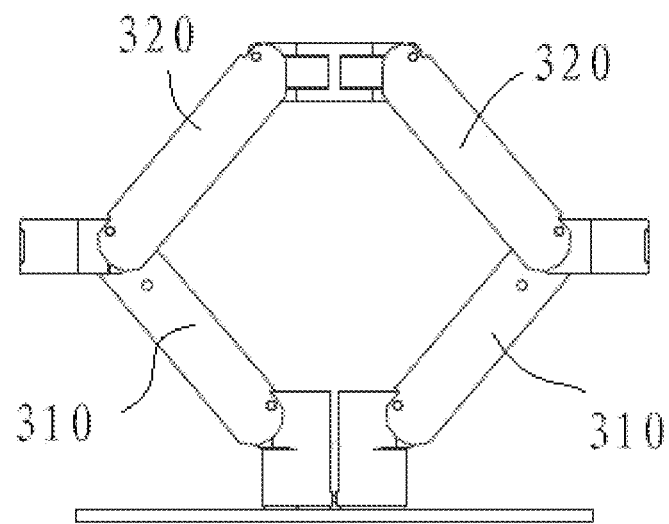
Figure 15B:
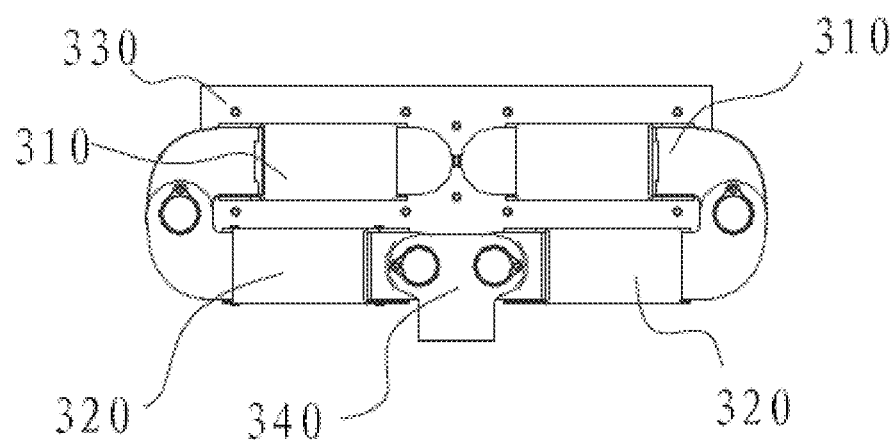
Figure 17A:
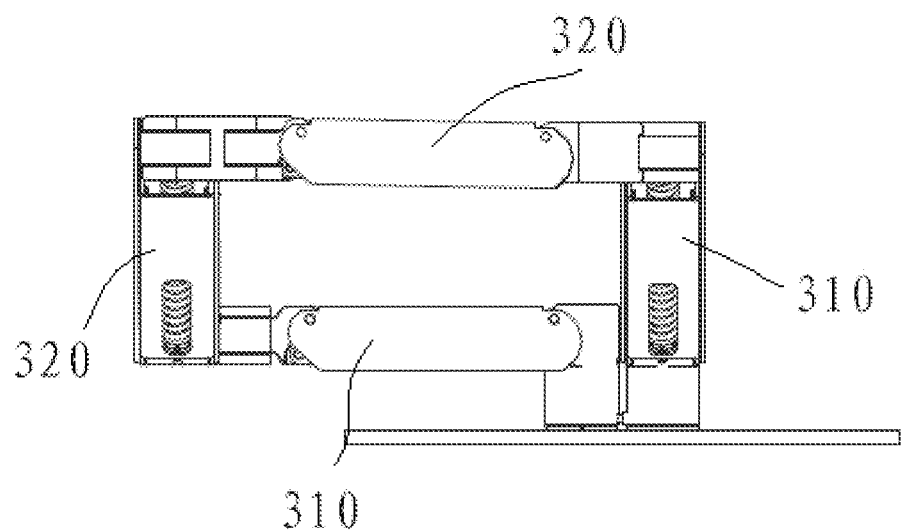
Figure 17B:
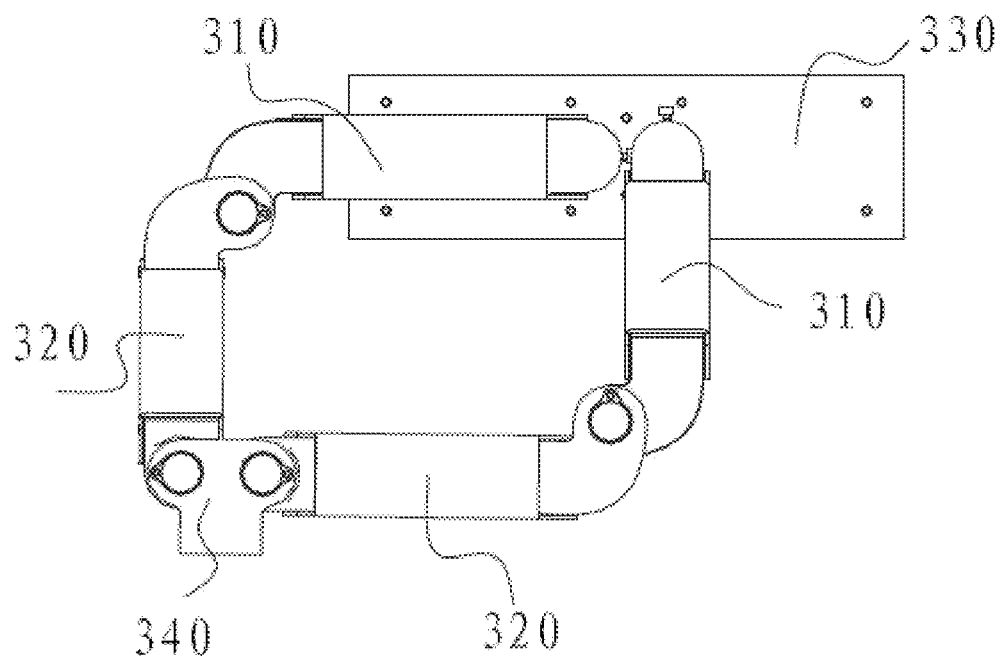
Figure 18A:
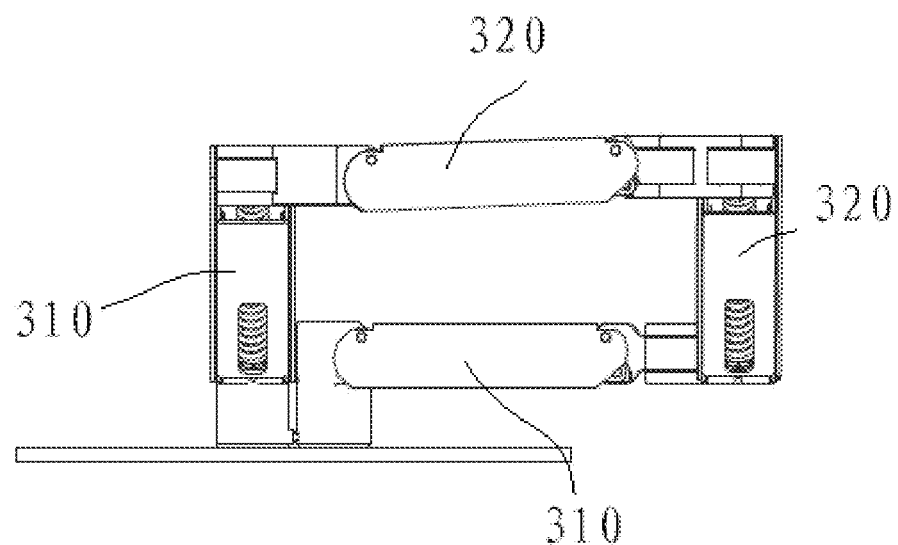
Figure 18B:
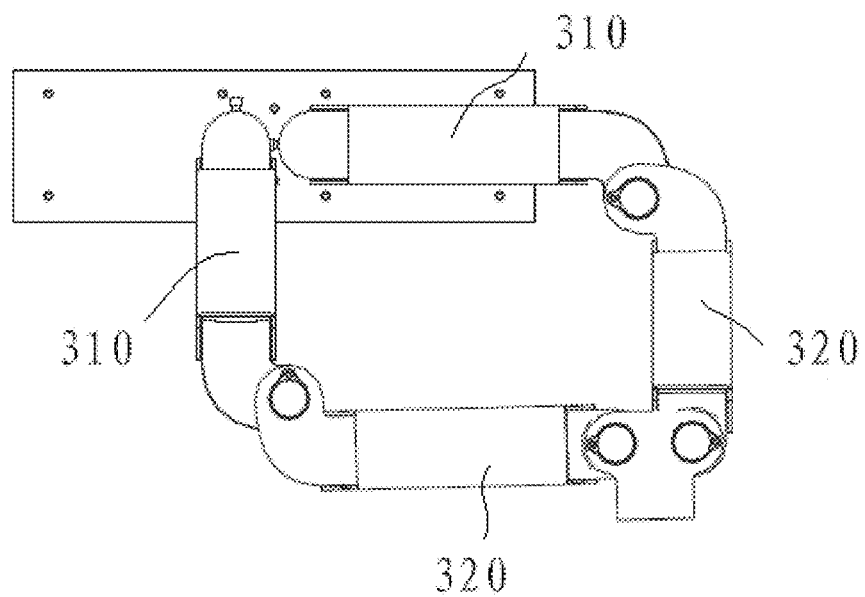

Specifically, FIGS. 11a and 11b schematically show the floating mechanism 300 that is in the lowermost horizontal plane and completely retracted. FIGS. 12a and 12b schematically show the floating mechanism 300 that is in the lowermost horizontal plane and extended forward (toward the front, that is, downward in FIG. 12b). FIGS. 13a and 13b schematically show the floating mechanism 300 that is in the lowermost horizontal plane and extended to the left. FIGS. 14a and 14b schematically show the floating mechanism 300 that is in the lowermost horizontal plane and extended to the right. FIGS. 15a and 15b schematically show the floating mechanism 300 in which the first rising-and-lowering mechanism 310 and the second rising-and-lowering mechanism 320 are raised right above. FIGS. 16a and 16b schematically show the floating mechanism 300 in which the first rising-and-lowering mechanism 310 and the second rising-and-lowering mechanism 320 are raised forward and upward. FIGS. 17a and 17b schematically show the floating mechanism 300 in which the first rising-and-lowering mechanism 310 and the second rising-and-lowering mechanism 320 are raised to the left and upward. FIGS. 18a and 18b schematically show the floating mechanism 300 in which the first rising-and-lowering mechanism 310 and the second rising-and-lowering mechanism 320 are raised to the right and upward.

Figures 19A, 19B, 19C, 19D:
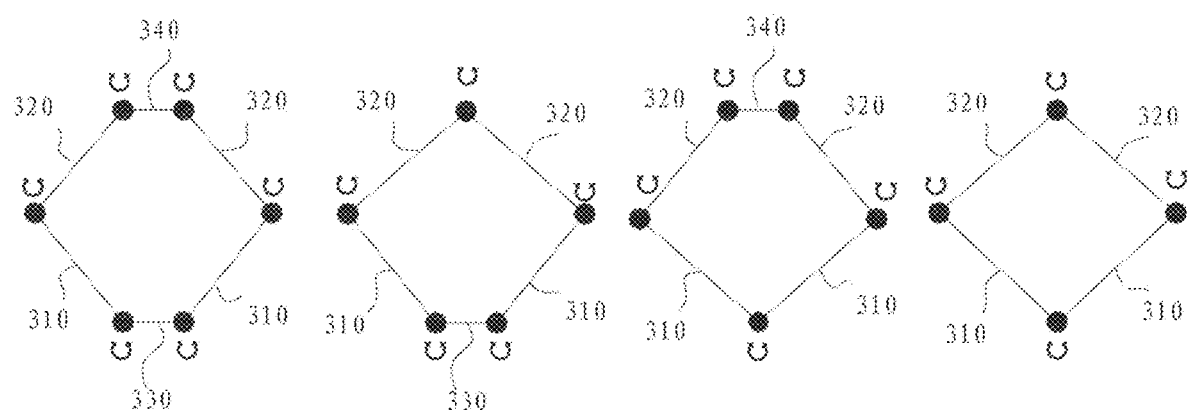

In addition, referring to FIG. 19a, in the structures shown above, the two connection rod assemblies may be installed on different rotation shafts in the fixation seat 340 and the mounting seat 330. In other embodiments, the floating mechanism 300 may also be modified as follows.

In variation 1, referring to FIG. 19b, the rotating structures of the two second rising-and-lowering mechanisms 320 with the fixation seat 340 may be arranged on the same rotation shaft.

In variation 2, referring to FIG. 19c, the rotating structures of the two first rising-and-lowering mechanisms 310 with the mounting seat 330 may be arranged on the same rotation shaft.

In variation 3, referring to FIG. 19d, the rotating structures of the two first rising-and-lowering mechanisms 310 with the mounting seat 330 may be arranged on the same rotation shaft, and the rotating structures of the two second rising-and-lowering mechanisms 320 with the fixation seat 340 may be arranged on the same rotation shaft.

Referring to FIG. 20a, in the two connection rod assemblies provided in one embodiment, the connection ends of the two first rising-and-lowering mechanisms 310 to be connected with the second rising-and-lowering mechanisms 320 (or the connection ends of the second rising-and-lowering mechanism 320 to be connected with the first rising-and-lowering mechanisms 310) may be arranged away from each other. That is, when the first rising-and-lowering mechanism 310 and the second rising-and-lowering mechanism 320 in the same connection rod assembly are retracted, the connection ends will be moved outward, as shown in FIG. 11b.

Referring to FIG. 20b, in the two connection rod assemblies provided in one embodiment, the connection ends of the two first rising-and-lowering mechanisms 310 to be connected with the second rising-and-lowering mechanisms 320 (or the connection ends of the second rising-and-lowering mechanism 320 to be connected with the first rising-and-lowering mechanisms 310) may be arranged close to each other. That is, when the first rising-and-lowering mechanism 310 and the second rising-and-lowering mechanism 320 in the same connection rod assembly are retracted, the connection ends will be moved inward, as shown in FIG. 12b.

Referring to FIGS. 11a and 11b, in one embodiment, the first rising-and-lowering mechanism 310 and the second rising-and-lowering mechanism 320 may be connected to each other at a substantially flush state. That is, as shown in FIGS. 11a and 11b, when the first rising-and-lowering mechanism 310 and the second rising-and-lowering mechanism 320 are retracted to the lowest position, the first rising-and-lowering mechanism 310 and the second rising-and-lowering mechanism 320 are substantially flush on the horizontal plane.

Figure 21B:
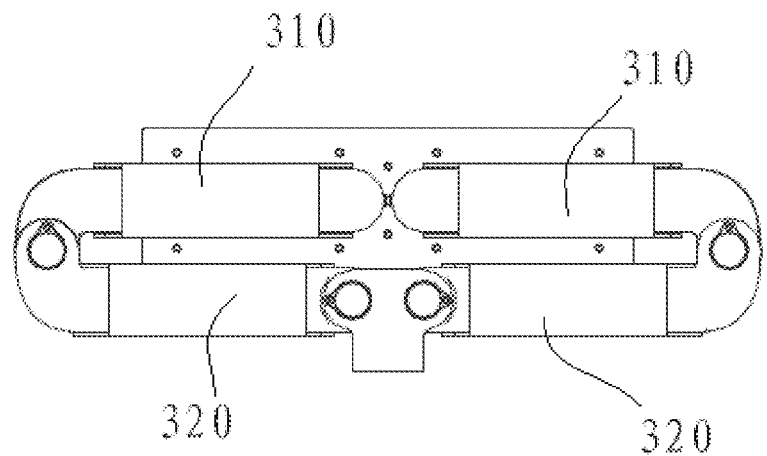
FIG. 21 schematically shows the floating mechanism in various states in another embodiment, where a and b represent schematic diagrams in different angles in the same state.

Referring to FIG. 21a and FIG. 21b, in order to reduce the horizontal space occupied by the first rising-and-lowering mechanism 310 and the second rising-and-lowering mechanism 320 arranged flush in the horizontal plane, in one embodiment, the first rising-and-lowering mechanism 310 and the second rising-and-lowering mechanism 320 may be arranged in vertical direction, that is, as shown in FIGS. 21a and 21b, when the first rising-and-lowering mechanism 310 and the second rising-and-lowering mechanism 320 are retracted to the lowest position, the first rising-and-lowering mechanism 310 and the second rising-and-lowering mechanism 320 are at different levels, but not flushed horizontally.

In the floating mechanism 300 shown in the embodiments, the first rising-and-lowering mechanism 310 may be rotatably connected to the mounting seat 330 through the rotation pair, and the mounting seat 330 may be connected to the first component. The second rising-and-lowering mechanism 320 may be rotatably connected to the first rising-and-lowering mechanism 310, the first connection seat 314 may be rotatably connected to the first rising-and-lowering mechanism 310 through the third rotation pair, and the second component may be rotatably connected to the second rising-and-lowering mechanism 320 through the fixation seat 340. This way, there are more degrees of freedom of movement between the second component connected to the second rising-and-lowering mechanism 320 and the first component, and the movement in multiple directions or in multiple degrees of freedom between the first component and the second component can be simultaneously achieved. For example, in one embodiment, the translation to the back and forth, the translation to left and right, the rotation to the left and right and the lifting of the second component relative to the first component can be simultaneously achieved. The combined effect of these movements in multiple directions or in multiple degrees of freedom achieved simultaneously enable the second component to move freely relative to the first component in any movement path to any position in a certain spatial range which is at a distance from the first component.

The first component and the second component connected by the floating mechanism 300 may be respectively the main body 100, the control panel 200 or the display 400, or any other suitable components that are desired to be connected by the floating mechanism 300. Moreover, both the first rising-and-lowering mechanism 310 and the second rising-and-lowering mechanism 320 have a lifting function, so that the position of the floating mechanism 300 can be changed more flexibly. In the floating mechanism 300, the rising-and-lowering mechanism and the rotation structure may be designed as an integrated linkage. Therefore, the linkage is better, the response is rapid, the occupied space is small, and the operation range is large.

Various embodiments of the present disclosure have been described in the foregoing. However, it should be understood that the embodiments described in the foregoing are not strictly separated. On the contrary, some or all features in one or more embodiments can be combined with some or all features in another or other embodiments according to the needs of the actual situation, as long as these features will not interfere with each other and the basic physical laws will not be violated.

The present disclosure has been described with reference to the specific embodiments. However, it is only used to facilitate the understanding to, but not limit, the present disclosure. For those of ordinary skill in the art, based on the concepts of the present disclosure, the specific embodiments above may be modified.

The invention claimed is:

1. An ultrasound diagnostic apparatus comprising a main body, a control panel and a display, and further comprising a first connection rod assembly and a second connection rod assembly connected between a first component and a second component, wherein, the first component and the second component are any two of the control panel, the main body and the display, and each connection rod assembly comprises:
   a first support seat connected to the first component through a sixth rotation pair and being able to be rotated around a sixth rotation axis relative to the first component through the sixth rotation pair;
   a first connection arm, wherein one end of the first connection arm is connected to the first support seat through a first rotation pair and is able to be rotated around a first rotation axis relative to the first support seat through the first rotation pair;
   a first connection seat, wherein the other end of the first connection arm is connected to the first connection seat through a second rotation pair and is able to be rotated around a second rotation axis relative to the first connection seat through the second rotation pair;
   a second connection seat connected to the first connection seat through a third rotation pair and being able to be rotated around a third rotation axis relative to the first connection seat through the third rotation pair;
   a second connection arm, wherein one end of the second connection arm is connected to the second connection seat through a fourth rotation pair and is able to be rotated around a fourth rotation axis relative to the second connection seat through the fourth rotation pair; and
   a second support seat, wherein the other end of the second connection arm is connected to the second support seat through a fifth rotation pair and is able to be rotated around a fifth rotation axis relative to the second support seat through the fifth rotation pair;
   wherein the second support seat is connected to the second component through a seventh rotation pair and is able to be rotated around a seventh rotation axis relative to the second component through the seventh rotation pair.

2. The ultrasound diagnostic apparatus of claim 1, wherein, the first support seat of the first connection rod assembly and the first support seat of the second connection rod assembly are separate, and are connected to the first component at a predetermined distance; and/or, the second support seat of the first connection rod assembly and the second support seat of the second connection rod assembly are separate, and are connected to the second component at a predetermined distance.

3. The ultrasound diagnostic apparatus of claim 1, wherein the first rotation axis and the second rotation axis are parallel to each other.

4. The ultrasound diagnostic apparatus of claim 1, wherein the fourth rotation axis and the fifth rotation axis are parallel to each other.

5. The ultrasound diagnostic apparatus of claim 1, wherein the third rotation axis and the second rotation axis are perpendicular to each other.

6. The ultrasound diagnostic apparatus of claim 1, wherein the third rotation axis and the fourth rotation axis are perpendicular to each other.

7. The ultrasound diagnostic apparatus of claim 1, wherein the sixth rotation axis and the third rotation axis are parallel to each other.

8. The ultrasound diagnostic apparatus of claim 1, wherein the seventh rotation axis and the third rotation axis are parallel to each other.

9. The ultrasound diagnostic apparatus of claim 1, wherein the third rotation axis of the first connection rod assembly and the third rotation axis of the second connection rod assembly are parallel to each other.

10. The ultrasound diagnostic apparatus of claim 1, wherein the sixth rotation axis of the first connection rod assembly and the sixth rotation axis of the second connection rod assembly are parallel to each other.

11. The ultrasound diagnostic apparatus of claim 1, wherein the seventh rotation axis of the first connection rod assembly and the seventh rotation axis of the second connection rod assembly are parallel to each other.

* * * * *